(12) United States Patent
Nakamura

(10) Patent No.: US 9,265,729 B2
(45) Date of Patent: Feb. 23, 2016

(54) NANOFUNCTIONAL SILICA PARTICLES AND MANUFACTURING METHOD THEREOF

(75) Inventor: Michihiro Nakamura, Tokushima (JP)

(73) Assignee: THE UNIVERSITY OF TOKUSHIMA, Tokushima-shi (JP)

(*) Notice: Subject to any disclaimer, the term of this patent is extended or adjusted under 35 U.S.C. 154(b) by 713 days.

(21) Appl. No.: 12/734,968

(22) PCT Filed: Dec. 8, 2008

(86) PCT No.: PCT/JP2008/072285
§ 371 (c)(1),
(2), (4) Date: Jul. 30, 2010

(87) PCT Pub. No.: WO2009/072657
PCT Pub. Date: Jun. 11, 2009

(65) Prior Publication Data
US 2010/0310872 A1    Dec. 9, 2010

(30) Foreign Application Priority Data
Dec. 6, 2007   (JP) ................................ 2007-316466

(51) Int. Cl.
| | |
|---|---|
| B32B 5/00 | (2006.01) |
| A61K 49/00 | (2006.01) |
| H01F 1/00 | (2006.01) |
| A61K 9/16 | (2006.01) |
| C08G 77/06 | (2006.01) |
| C08G 77/28 | (2006.01) |
| C08G 77/20 | (2006.01) |
| C08G 77/26 | (2006.01) |

(52) U.S. Cl.
CPC .............. *A61K 9/1676* (2013.01); *C08G 77/06* (2013.01); *C08G 77/28* (2013.01); *C08G 77/20* (2013.01); *C08G 77/26* (2013.01); *Y10T 428/2995* (2015.01)

(58) Field of Classification Search
None
See application file for complete search history.

(56) References Cited

U.S. PATENT DOCUMENTS

| | | | | |
|---|---|---|---|---|
| 4,775,520 | A | * | 10/1988 | Unger et al. .................. 423/335 |
| 2003/0124564 | A1 | * | 7/2003 | Trau et al. .......................... 435/6 |
| 2004/0101822 | A1 | * | 5/2004 | Wiesner et al. ................... 435/5 |
| 2006/0068203 | A1 | * | 3/2006 | Ying et al. .................... 428/403 |

(Continued)

OTHER PUBLICATIONS

Self-Assembled Hybrid Nanoparticles for Cancer-Specific Multimodal Imaging by Jason S. Kim et al. of Departments of Chemistry and Radiology, University of North Carolina, Published on Web Jun. 30, 2007, JACS Communications (J.Am.Chem.Soc. 2007, vol. 129, p. 8962-8963).

(Continued)

*Primary Examiner* — Ronak Patel
(74) *Attorney, Agent, or Firm* — Masuvalley & Partners

(57) ABSTRACT

Provided are nanofunctional silica particles having excellent functionality and quality, and capable of being mass-produced at low costs. According to the present invention, there are provided nanofunctional silica particles including a coating layer containing one or more silica compounds selected from the group consisting of mercaptopropyl trimethoxysilane (MPS), mercaptopropyl triethoxysilane (MPES), mercaptopropyl methyldimethoxysilane (MPDMS), trimethoxy [2-(7-oxabicyclo[4.1.0]-hept-3-yl)ethyl]silane (EpoPS), thiocyanatopropyl triethoxysilane (TCPS), acryloxypropyl trimethoxysilane (ACPS), and aminopropyl trimethoxysilane (APS); and functional particles in the coating layer, and being used in imaging, assay, diagnosis, treatment or the like, medicine or bioresearch.

9 Claims, 23 Drawing Sheets

(56) References Cited

U.S. PATENT DOCUMENTS

2008/0241044 A1\* 10/2008 Kuebelbeck ............... 423/335
2008/0305489 A1\* 12/2008 Thomas et al. ............... 435/6

OTHER PUBLICATIONS

Hybrid Silica Nanoparticles for Multimodal Imaging by William J. Rieter et al., Published on Web (www.angewandte.org), Wiley-VCH Verlag CmbH & Co. KGaA, Weinheim (Angew. Chem. Int. Ed. 2007, vol. 46, p. 3680-3681).
Synthesis of Water-Soluble and Functioinalized Nanoparticles by Silica Coating by Nikhil R. Jana et al., Institute of Bioengineering and Nanotechnology, 31 Biopolis Way, The Nanos, Singapore 138669, Published on Web Sep. 18, 2007, American Chemical Society, (Chem. Mater., vol. 19, No. 21, 2007 p. 5074-5082).

\* cited by examiner

NANOFUNCTIONAL SILICA PARTICLES AND MANUFACTURING METHOD THEREOF

This application claims priority under 35 U.S.C. §371 as a National Stage application of PCT application Serial No. PCT/JP2008/072285, filed Dec. 8, 2008, entitled "Nanofunctional silca particles and manufacturing method thereof", which claims priority to Japanese Patent Application No. P 2007-316466 filed on Dec. 6, 2007, which are incorporated herein by reference.

TECHNICAL FIELD

This invention relates to silica nanoparticles having a double structure wherein the nanoparticle is roughly divided into a region of an outer layer or shell occupying a surface layer and a region of an inner layer or core occupying a layer beneath the surface layer, and in particular relates to a method for manufacturing novel silica nanoparticles that exhibit multifunctionality, and a usage thereof. More specifically, the present invention relates to nanofunctional silica particles which have remarkably better characteristics than conventional silica particles, contain a functional material in the surface thereof, and/or the shell region thereof, and/or the core region thereof, and have a nature of the functional material together. Moreover, a manufacture of the nanofunctional silica particles is also disclosed.

BACKGROUND ART

Various kinds of techniques about a method for manufacturing silica particles or silica spheres, and a usage thereof have been researched and developed all over the world. Some parts thereof have been already put into practice in bioassays, and others. For the synthesis thereof, TEOS (tetraethylorthosilane, which will be abbreviated to "TEOS" hereinafter) has been conventionally used as a starting material. However, surface layers of particles wherein this material, TEOS, is used are low in chemical reactivity, that is, in bonding capability to foreign proteins or nucleic acids; therefore, an attempt has been made for activating the particles by the introduction of an acceptor group by use of a silica compound different from the material TEOS (Patent Document 1). Known are, for example, the introduction of a SH group by use of MPS (mercaptopropyl ethoxysilane, or 3-mercaptopropyltrimethoxysilane, which will be abbreviated to (MPS)), and that of some other (introduced groups), such as tetraethoxysilane (OH group), or aminopropylethoxysilane ($NH_2$ group). However, these activated silica particles have a double structure composed of an inner shell made of TEOS and an outer shell or surface layer made of an acceptor group, and time, labor and other costs required for the manufacture thereof are high. Moreover, the particles are not easily produced based on the selection of a silica compound wherein the number of bonding sites for forming silica network (Si—O), the number of which is four in TEOS, is three or less (such as MPS). Actually, known is a technique of pre-treating MPS with hydrochloric acid alone (or a mixed liquid of hydrochloric acid and cetylmethylammonium chloride) (at room temperature for 2 to 5 days), adding an aqueous ammonia solution thereto, mixing the components with each other, and further allowing the reactive components to react with each other at room temperature for 2 days, thereby yielding MPS particles (Patent Document 2). However, this technique gives high manufacturing costs, and has complicated manufacturing steps, and further requires considerable days for manufacturing the particles. Additionally, the size (particle diameter) of the manufactured particles is not easily adjusted.

The MPS particles yielded by the method in Patent Document 2 are high in the property that pores have been formed, so that the particles have an advantage that the surface area is enlarged by the formed pores. However, the method is not advantageous in a case where the particles aim for taking in a functional material, or in a case where the particles aim for being used in a quantitative experiment about DNA, a protein or the like. A reason therefor is that as the property that pores have been formed is lower, the number of inner sites where a functional material can be arranged is larger to give a favorable result (a higher fluorescence intensity per particle). Another reason therefor appears to be as follows: about particles having many pores as in Patent Document 2, the effective adhesive area thereof, to which DNA or a protein can adhere, does not depend only on the surface area based on the diameters of the particles, and is varied in accordance with the size or the number of the pores, or the positions thereof; thus, the parameter of the adhesive area is diversified so that a problem is caused for quantitation. Thus, it is required that silica particles having no pores are manufactured.

The present inventors suggest the following in Patent Document 3: silica particles that overcome defects of the conventional silica particles including TEOS particles, that is, high manufacturing costs, low chemical reactivity (bonding capability to foreign proteins or nucleic acids) and other problems, are excellent in functionality and quality and are further able to be mass-produced at low costs; and a manufacturing method thereof. This manufacturing method makes it possible to arrange or incorporate a functional material into surface layers of silica particles or the insides thereof and stabilize the material, thereby allowing the silica particles to have surface layer functionalizing capability or inside functionalizing capability. Examples of the functional material used therein include chemical agents, fluorescent materials, proteins, peptides, nucleotides, nucleotide analogues, oligonucleotides, oligonucleotide analogues and sugar chains; but, the material is not limited thereto. However, in the silica particles invented by the present inventors, the incorporation of a functional material, such as gold colloid or magnetic material, is not conducted. Thus, for the purpose of enlargement of the usage thereof, silica particles having a greater multifunctionality have been desired.

In recent years, the development of biotechnology or nanotechnology has been giving a change to nano medical treatment, imaging or other medical techniques. In conventional imaging, a single probe has been used only in a single estimating method. For example, a magnetic material is used as an imaging agent in an MRI; however, the material is not usually used in any detailed observation with a microscope. However, by technical development in recent years, development of a multifunctional probe having a multimodal function has been desired, and has been advanced, which can be used commonly in vivo and in vitro, or in macro-observation or micro-observation, and further in various machines such as a CT, a PET, and an MRI (Non-Patent Documents 1 and 2). Moreover, a development of multifunctional particles has been desired which give a treatment effect to a multimodal imaging probe and can be used consistently from diagnosis to treatment. Such multifunctional particles would give an innovation to medical treatment and therefore, it is considered that patients' burdens can be relieved, and high treatment effects can be obtained.

However, through the existing imaging agent, macro-observation can be attained, but micro-observation, wherein a microscope is used, cannot be attained. Additionally, a fluorescently labeled antibody used in observation with a microscope cannot be observed through a CT or an MRI. Development competitions of particles having both of a multimodal imaging effect and a treatment effect have been advanced all over the world. However, the particles have a technical problem. Thus, the particles have not yet been completed.

Patent Document 1: WO 2006/070582 Pamphlet
Patent Document 2: WO 2003/002633 Pamphlet
Patent Document 3: Japanese Patent Application No. 2006-160107
Non-Patent Document 1: Journal of America Chemical Society, 2007, 129, 8962-8963
Non-Patent Document 2: Angewandte Chemie International Edition, 2007, 46, 3680-3682

DISCLOSURE OF THE INVENTION

Problems to be Solved by the Invention

An Object of the present invention is to solve problems as described above in the prior art. In other words, an object of the invention is to create function-fused type nanofunctional silica particles wherein an existent functional material is incorporated into silica particles which are better in functionality and quality than conventional silica particles including TEOS particles and which can be mass-produced at low costs, thereby making the function thereof higher, and further problems of the conventional particles are overcome to create new values.

Furthermore, an object thereof is to provide a multifunctional probe and a probe for treatment that can each be used commonly in vivo and in vitro, or in micro-observation and macro-observation, and further in various machines such as a CT, a PET and an MRI by realizing a functional fusion of excellent surface layer functionalizing capability and inside functionalizing capability of organosilica particles, which have been developed in recent years, and some other functional materials, whereby the probes each have a multimodal function.

Means for Solving the Problems

Accordingly, the following are provided by the present invention:

The nanofunctional silica particles of the present invention have (A1) a shell made mainly of silica obtained from one or more organosilica compounds selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TCPS), acryloxypropyl trimethoxysilane (ACPS), and aminopropyl trimethoxysilane (APS); and, in the shell, (A2) a core having a diameter of 2 to 200 nm and containing one or more species of a magnetic material, gold colloid, a quantum dot, gadolinium-containing particles, and an imaging functional material-containing liquid.

The nanofunctional silica particles of the present invention may have (A1) a shell made mainly of silica obtained from one or more organosilica compounds selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TCPS), acryloxypropyl trimethoxysilane (ACPS) and aminopropyl trimethoxysilane (APS), and (A2) aminopropyl triethoxysilane (APES); and, in the shell, (A3) a core having a diameter of 2 to 200 nm and containing one or more species of a magnetic material, gold colloid, a quantum dot, gadolinium-containing particles, and an imaging functional-material-containing liquid.

A functional compound may be held in the surface of the shell of the nanofunctional silica particles, and/or in the shell thereof, and/or in the core thereof. A difference in surface potential between the shell and the functional compound itself is preferably 3 mV or more. The functional compound held in the surface of the shell, and/or in the shell, and/or in the core is preferably selected from the group consisting of a functional group, a fluorescent material, a protein, a nucleotide, an oligonucleotide, a sugar chain, a bioactive material, an imaging agent and a chemical agent, and combinations of two or more thereof. The nanofunctional silica particles each preferably have a particle diameter of 3 to 500 nm.

Preferably, the fluorescent material is selected from the group consisting of rhodamine red, fluorecein, hexanoic acid-6-(tetramethylrhodamine-5-carboxamide), hexanoic acid 5-(tetramethylrhodamine-5-carboxamide), Alexa Fluor 647, DY 635, DY 485, DY 495, DY 505, and trisdichlororuthenium (II) hexahydrate, and the fluorescent material is held alone or in a state where the material is bonded to a compound selected from N-hydroxysuccinimide (NHS), isothiocyanate (ITC), and maleimide.

The functional compound held in the surface of the shell is selected from the group consisting of a functional group, a fluorescent material, a protein, a nucleotide, an oligonucleotide, a sugar chain, a bioactive material, an imaging agent and a chemical agent, and combinations of two or more thereof and preferably the functional compound is held in a state that molecular level species of only the selected material(s) are bonded to each other, in a state where the selected material(s) and an added coupling agent are bonded to each other, or in a state where the selected material(s) is/are bonded to a compound selected from N-hydroxysuccinimide (NHS), isothiocyanate (ITC), and maleimide.

Preferably, a material having a cell damage activating function is held in the surface of the shell, and/or in the shell, and/or in the core, and the material is specifically a material which is irradiated with light to exhibit the cell damage activating function.

Additionally, the present invention provides a method for manufacturing the nanofunctional silica particles. Specifically, the method includes steps for:

(A1) (a) preparing a mixed liquid of an organosilica compound, a functional material, and an aqueous ammonia solution; or preparing a mixed liquid of an organosilica compound, a functional material, a functional compound, and an aqueous ammonia solution, and (b) allowing the organosilica compound and the aqueous ammonia solution to react with each other at a predetermined temperature, wherein (A2) the organosilica compound is one or more selected from the group consisting of mercaptopropyl trimethoxysilane (MPS), mercaptopropyl triethoxysilane (MPES), mercaptopropyl methyldimethoxysilane (MPDMS), trimethoxy [2(7-oxabicyclo[4.1.0]-hept-3-yl)ethyl]silane (EpoPS), thiocyanatopropyl triethoxysilane (TcPS), acryloxypropyl trimethoxysilane (ACPS) and aminopropyl trimethoxysilane (APS), (A3) the functional material is one or more species selected from the group consisting of a magnetic material, gold colloid, a quantum dot, gadolinium-containing particles, and an imaging functional material-containing liquid, and (A4) the aqueous ammonia solution and conditions for the temperature in the steps (a) and (b) are adjusted to satisfy the following:

(i) the temperature is high temperature (in the temperature range of 80 to 100° C.), and (ii) the solution has a high ammonia concentration (the solution gives a final concentration of 25% or more).

A method for manufacturing the nanofunctional silica particles includes steps for:

(A1) (a) preparing a mixed liquid of organosilica compounds, a functional material, and an aqueous ammonia solution; or preparing a mixed liquid of organosilica compounds, a functional material, a functional compound, and an aqueous ammonia solution, and (b) allowing the organosilica compounds and the aqueous ammonia solution to react with each other at a predetermined temperature, wherein (A2) the organosilica compounds are one or more selected from the group consisting of mercaptopropyl trimethoxysilane (MPS), mercaptopropyl triethoxysilane (MPES), mercaptopropyl methyldimethoxysilane (MPDMS), trimethoxy [2-(7-oxabicyclo[4.1.0]-hept-3-yl)ethyl]silane (EpoPS), thiocyanatopropyl triethoxysilane (TcPS), acryloxypropyl trimethoxysilane (ACPS) and aminopropyl trimethoxysilane (APS), and aminopropyl triethoxysilane (APES), (A3) the functional material is one or more species selected from the group consisting of a magnetic material, gold colloid, a quantum dot, gadolinium-containing particles, and an imaging functional material-containing liquid, and (A4) the aqueous ammonia solution and conditions for the temperature in the steps (a) and (b) are adjusted to satisfy the following:

(i) the temperature is high temperature (in the temperature range of 80 to 100° C.), and (ii) the solution has a high ammonia concentration (the solution gives a final concentration of 25% or more).

(Nanofunctional Silica Particles of the Present Invention)

The nanofunctional silica particles and the manufacturing method thereof according to the present invention have unprecedented features and characteristics described below in connection with advantageous effects thereof.

(a) The features of the nanofunctional silica particles are as follows:

(1) The functional materials are located in the nanofunctional silica particles, in the inner layers thereof or in the core regions thereof, and the upper layers or outer layers of the organosilica compound can be morphologically distinguished from the shell regions. In other words, the structure of each of the silica particles can be roughly divided into the shell region and the core region.

(2) The nanofunctional silica particles have functions that the contained functional materials have.

(3) The nanofunctional silica particles can hold, in the surfaces thereof, and/or in the shells thereof, and/or in the cores thereof, the functional compound, which is a fluorescent colorant, a chemical agent or the like.

(4) The particles are high in capability of adsorbing a protein, a nucleic acid or the like by acceptor groups in the surface layers or surfaces of the organosilica compound.

(5) The particles can allow an antigen, an antibody, an enzyme or the like to be effectively bonded to the surfaces thereof in a state where the function of the substance is kept without denaturing the substance (inactivating the activity or the function thereof).

(6) Antigen-antibody reaction can be conducted in the surface layers.

(7) A substance can be detected on the surfaces of the particles with high sensitivity.

(8) The particles can allow a chemical material, such as a protein, nucleic acid or colorant, to be bonded on the surface layers thereof by aid of a conjugating reagent.

(9) Aggregation resulting from the production of the particles or modification of the surface layers is less caused.

(10) With respect to the diameter of the particles and the form thereof, the particles can be adjusted into a form such that the functional materials constitute the cores and into a size from nano-sizes to micron-sizes by the adjustment of the silica layers.

(11) When a chemically conjugating material is bonded to the silica layers, the efficiency of adsorbing a protein or the like is drastically improved.

(12) Under a condition that the present particles are irradiated with excited light, the proliferation activity of cells around the particles is lowered. Accordingly, the particles have not only an imaging function but also a cell damaging function under the condition of the irradiation with excited light.

(b) The features of the manufacturing method are as follows:

(1) The period required for the manufacture is a very short period (of 1 to 12 hours).

(2) The number of reagent species required for the manufacture is small (a surfactant, hydrochloric acid and the like are not used), and the particles can be mass-produced through a production process wherein reaction is carried out at one stage or in one step. A container, a tube, a flask, tank or the like that is required for the manufacture is a single tool corresponding to the scale of the manufacture.

Effect of the Invention

The function of conventional silica particles is improved, and the usage thereof is diversified and enlarged in some other manners, thereby increasing additional values of the silica particles. Provided are nanofunctional silica particles that are used in imaging, assay, diagnosis, treatment or the like, and give an innovational technical progress to medicine or bioresearch.

BEST MODE FOR CARRYING OUT THE INVENTION

Definition of Terms

The term "nanoparticles" refers to particles having a diameter in the order of several nanometers. These particles are obtained by a matter that atoms or molecules gather, react with each other, or grow to be stabilized or arranged so that the atoms or the molecules turn into a cluster, and then the cluster grows further. In the present specification, terms "silica particle(s)", "silica sphere(s)", "silica nanoparticle(s)" and "NP(s)" are each used under the condition that the terms are exchangeable between each other, and each refer to a particulate material produced from a "silica compound".

The term "silica compound" denotes, when used in the specification, a compound having a central atom of silicon Si. The term intends a substance that functions as a supply source for providing, when nanoparticles are produced, silicon for the particles. The silica compound is, for example, a compound provided in the form of $SiR_1R_2R_3R_4$ wherein $R_1$, $R_2$, $R_3$ and $R_4$ are each an arbitrary organic group. More preferably, the silica compound denotes mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TCPS), acryloxypropyl trimethoxysilane (ACPS), aminopropyl trimethoxysilane (APS) and aminopropyl triethoxysilane (APES); and compounds having physical/chemical properties equivalent to those of these compounds. This is also clear from Patent Document 3.

A method for producing a nano-scale material is generally classified into a bottom-up process and a top-down process. The former, that is, the bottom-up process is a process wherein while atoms or molecules are allowed to interact with each other in a physical or chemical way and react with each other, the scale thereof is made large. A control thereof can be attained in an atomic or molecular order. Examples of this bottom-up process include laser radiation process (thin film growing process), self-organization process, chemical vapor deposition process, Buruburu process, coagulation sedimentation process, and combinatorial chemistry process. The top-down process is a process of breaking a material in a bulk form, or processing the material to be made fine. Examples thereof include lithographic process and etching process. For the synthesis of nanoparticles, Buruburu process, gas phase process, spraying process and others are conducted. Among these processes, Buruburu process is a process of drying a sol-state liquid to be gelatinized, thereby synthesizing a solid (Stober, W.; Fink, A.; Bohn, E. J. Colloid Interface Sci., 1968, 26, 62-69). In order to synthesize the nanoparticles of the present invention, the sol-gel process (Stober process) is used. In this Buruburu process, particles are produced at room temperature in a particle producing step thereof in a conventional way. In the method of the invention for manufacturing nanofunctional silica particles, the term "high temperature condition" denotes a reaction condition in the temperature range of 70 to 100° C., preferably 80 to 100° C., more preferably 90 to 100° C.

In the method of the present invention for manufacturing nanofunctional silica particles, the term "high ammonia condition" denotes that the concentration of a prepared aqueous ammonia solution is 20% or more, preferably from 20 to 30%, from 25 to 30% or from 26 to 28%, more preferably 27% as a final concentration thereof. In the method, a middle ammonia concentration denotes that the concentration of a prepared aqueous ammonia solution is 10% or more and less than 20% as a final concentration thereof. A low ammonia concentration denotes that the concentration of a prepared aqueous ammonia solution is 2% or more and less than 5% as a final concentration thereof. In connection with the "high ammonia condition", in the case of using ammonia in a sol-gel method, an ammonia concentration of several percentages is used in conventional methods; and the "high ammonia condition" used in the present invention, as described above, is not used. It is understood that one reason of this matter is as follows: TEOS, which has been hitherto used to produce nanoparticles, tends to dislike high ammonia in the formation of particles. Actually, also from results of inspections made by the present inventors themselves, it has been determined that TEOS dislikes high ammonia in the formation of particles. The inventors have obtained a result that particles are not completely formed, aggregation is caused, or other bad results are caused (not reported). Accordingly, in light of technical common knowledge, it is a surprising result that these conditions are used in the method of the present invention for manufacturing nanofunctional silica particles to make it promptly possible to synthesize nanoparticles having unprecedentedly excellent characteristics.

When the terms "lattice" and "silica network" in the nanoparticles of the present invention are used in the specification, the terms are used exchangeably between each other. The lattice of the particles denotes an internal structure of primary particles thereof, and intends a net-like three-dimensional structure formed through chemical bonds, typical examples of which include Si—O—, and Si—C—.

The term "particle diameter" is a barometer representing the size of a particle to be measured when used in the specification, and may be represented by the diameter of the particle. The "particle diameter" may be measured and determined by various techniques. The particle diameter may be determined by use of, for example, a transmission electron microscope.

In the specification, the term "acceptor group" denotes a functional group introduced into a silica particle or silica sphere. The relationship between a silica compound used to form a silica particle and an acceptor group introduced thereinto has, for example, a corresponding relationship described in the following table:

TABLE 1

| Silica compound | Acceptor group formed in silica sphere surface |
|---|---|
| Tetraethoxysilane | OH group |
| γ-Mercaptopropyl triethoxysilane | SH group |
| Aminopropyl triethoxysilane | NH2 group |
| 3-Thiocyanatopropyl triethoxysilane | SCN group |
| 3-Glycidyloxypropyl triethoxysilane | Epoxy group |
| 3-Isocyanatopropyl triethoxysilane | CNO group |

The term "fluorescent material" denotes, when used in the specification, a material emitting fluorescence when the material is excited by an external stimulus, such as an electromagnetic wave (for example, ultraviolet rays, X-rays, or an electron beam). Examples of this "fluorescent material" include rhodamine red, fluorecein, hexanoic acid-6-(tetramethylrhodamine-5-carboxamide), hexanoic acid-5-(tetramethylrhodamine-5-carboxamide), Alexa Fluor 647, DY 635, DY 485, DY 495, DY 505, and trisdichlororuthenium (II) hexahydrate. However, the fluorescence material is not limited thereto. This fluorescent material is present in the silica particles, for example, in a form as described in any one of the following items (1) to (4) although allowable forms are not limited thereto: (1) the material alone is contained in the particles; (2) a reaction obtained by reacting a substance wherein the fluorescent material is bonded to a compound selected from N-hydroxysuccinimide (NHS) and isothiocyanate (ITC), with 3-(aminopropyl)triethoxysilane is contained in the particles or is present in the surface layers in such a manner that the reaction product is bonded to their silica networks; (3) a reaction product obtained by reacting a substance wherein the fluorescence material is bonded to maleimide, with MPS is contained in the particles or is present in the surface layers in such a manner that the reaction product is bonded to their silica networks; or (4) a substance wherein the fluorescent material is bonded to maleimide reacts with the silica particles that contain a silica compound having a thiol, whereby the substance is present in the surface layers of the particles. These are also evident from Patent Document 3.

The term "surface layer functionalization" denotes, when used in the specification, that a functional material is arranged and stabilized into the surface layers of the silica particles of the present invention. The nature of object particles capable of attaining the surface layer functionalization is represented as surface layer functionalizing capability. In the specification, the term "being stabilized" denotes, for example, that provided is a physically/chemically stable state necessary for a matter that in silica particles, a functional material therein realizes, with reproducibility, a function desired in an environment wherein the material is used.

The term "inside functionalization" denotes, when used in the specification, that a functional material is incorporated and stabilized into the silica particles of the present invention. The nature of object particles capable of attaining the inside functionalization is represented as inside functionalizing capability.

In the specification, the term "functional material" denotes a material that can function by itself, and examples thereof include a magnetic material, gold colloid, a quantum dot, core silica particles, a cell, a cellar structure, a bioactive material, a catalyst, catalytic nanoparticles, and a functional compound-containing liquid. However, the functional material is not limited thereto.

In the specification, the term "magnetic material" denotes a material that can be magnetized easily, and desirably denotes a ferromagnetic material. Herein, a ferromagnetic material refers to a material that is magnetized intensely and exhibits hysteresis. Typical examples of the magnetic material include iron oxide, chromium oxide, cobalt, and ferrite. However, the magnetic material is not limited thereto.

In the specification, the term "gold colloid" denotes a substance wherein an aggregate of gold atoms is dispersed in a liquid phase or the like. Gold colloid can be directly observed with a scanning or transmission electron microscope. According to gold colloid, a protein such as an antibody can be non-covalently labeled, and the location thereof can be observed with an electron microscope. Gold colloid may be gold colloid having a size permitting plasmon resonance or an exothermic phenomenon based on plasmon resonance.

In the specification, the term "quantum dot" denotes an exciton wherein a potential box as fine as a three-dimensional quantum confinement is given is formed. The quantum dot may include a quantum dot emitting fluorescence.

In the specification, the term "core silica particles" means silica particles as cores each coated with a shell of an organosilica. In accordance with the kind of an organosilica to be used, the size of silica particles to be used, the distribution thereof, and whether particles which turns cores can be coated or not are varied. In a case where core particles cannot be directly coated with an organosilica having a desired functional group, the core particles may be beforehand coated with a different inorganic or organosilica. The coating makes it possible that after the above-mentioned "silica particles as cores" are formed, the core silica particles are coated with a desired organosilica.

About a specific example thereof, see Example 26, which will be described later.

The term "cell" used in the specification denotes an animal cell, a plant cell, mold, yeast, a colon *bacillus*, a hay *bacillus*, or the like. However, the cell is not limited thereto.

In the specification, the term "cellar structure" denotes a structure present in a cell. Specific examples thereof include a cell nucleus, a mitochondrion, a chloroplast, a Golgi body, a ribosome, and a cell membrane. However, the cellar structure is not limited thereto.

In the specification, the term "bioactive material" specifically denotes a virus, a prion, an antigen, an antibody, a toxin, a toxoid, or the like. However, the bioactive material is not limited thereto.

The term "functional compound" denotes, when used in the specification, a material taking charge of a physical, chemical or biological effect. The form thereof is any form as far as the material is a material having a site interacting with an object on which the material acts. Examples of the functional compound include a fluorescent material, a protein, a nucleotide, a nucleotide analogue, an oligonucleotide, an oligonucleotide analogue, sugars, a bioactive material, a colorant, a paint, an imaging agent and a chemical agent (for example, a photosensitive agent). However, the functional compound is not limited thereto. These matters are also evident from Patent Document 3.

In the specification, the term "functional compound-containing liquid" denotes a liquid substance containing the "functional compound" as described above. Specific examples of the "containing liquid" include solutions, colloid solutions, suspensions, emulsions, and other liquid substances.

The terms "protein", "polypeptide", "oligopeptide" and "peptide" used in the specification are used to have the same meaning in the specification. The terms each denotes an amino acid polymer having any length, and any modified product thereof. This polymer may be linear, branched, or cyclic. The amino acid may be a natural, non-natural, or modified amino acid. The terms may each denote materials that can be assembled into a complex of plural polypeptides. The terms may each denote a naturally- or artificially modified amino acid polymer. Examples of the modification include the formation of a disulfide bond, glycosylation, lipogenesis, acetylation, phosphorylation, and any other operation or modification (for example, bonding to a labeling component). This definition may also denote, for example, a polypeptide containing one or more analogues of amino acids (for example, a polypeptide containing a non-natural amino acid), a peptide-like compound (for example, peptoid), or some other modifications known in the art. A "protein" used in the organization material of the present invention is preferably a protein having an adaptive ratio to a host wherein the organization material is to be used. However, any protein may be used as far as the protein can be treated so as to be adapted to the host by biotechnological modification, chemical modification, or the like. Whether or not a certain protein is adaptive to a host, or whether or not a certain protein can be treated so as to be adapted to a host can be determined by administering the protein to the host, optionally restraining a side reaction such as immunorejection reaction, and observing whether or not the protein is fixed to the host. Typically, the protein having the above-mentioned adaptive ratio is a protein originating from the host, but is not limited thereto.

In the specification, the term "nucleotide" denotes a nucleoside wherein a sugar moiety is made into a phosphoric acid ester. The nucleotide may be DNA, RNA, or the like, and may be natural or non-natural. The nucleoside is a compound wherein a base and a sugar undergo N-glycoside bonding. The term "nucleotide derivative" or "nucleotide analogue" denotes a substance which is different from any naturally occurring nucleotide but has a function similar to that of an original nucleotide. Such derivative nucleotides and nucleotide analogues are well known in the art. Examples of the derivative nucleotides and the nucleotide analogues include phosphorothioate, phosphoramidate, methyl phosphonate, chiral methyl phosphonate, 2-O-methylribonucleotide, and peptide-nucleic acid (PNA). However, the derivatives or the analogues are not limited thereto. DNA may be cDNA, genome DNA, or synthesized DNA.

In the specification, the term "bioactive material" specifically denotes a hormone, a vitamin, an enzyme, or the like. However, the bioactive material is not limited thereto.

In the specification, the term "biomaterial" denotes any biogenic material. Examples of the material include a colon *bacillus*, and yeast. However, the material is not limited thereto.

In the specification, the term "chemically conjugating material" denotes a material capable of being bonded to an amino group of a protein and a thiol group of an organosilica compound to bond the protein onto particle surfaces. "Maleimide" or "a maleimide compound" include, as examples thereof, the following: 3-maleimidopropionic acid, N-(4-aminophenyl)maleimide, 1,2-bis(maleimido)ethane, N,N'-1,4-phenylenedimaleimide, N-(4-nitrophenyl)maleimide, N-bromomethyl-2,3-dichloromaleimide, N-[4-(2-benzimidazolyl)phenyl]maleimide, N-succinimidyl 4-maleimidobutyrate, N-cyclohexylmaleimide, 4-maleimidobutyric acid sulfo-N-succinimidyl ester, 1,2-bis(maleimido)ethane, and TFA/N+maleimide. When this is used, bonding to functional groups of the particle surfaces can be attained.

In the specification, the term "functional group" denotes a thiol group, a carboxyl group, an amino group, —SO3Na, —SO3H, an ethyl group, a methyl group, 4-(2-benzimidazolyl)phenyl], a phenyl group, a 4-nitrophenyl group, a chloro radical, a chlorophenyl group, a bromo radical, cyclohexane, succinimide ester, and maleimide; and groups containing one or more thereof.

Embodiments of this invention will be described in detail hereinafter. First, the production or manufacture of nanofunctional silica particles wherein MPS is used will be described.

(Multifunctional MPS Particles)

(a) Manufacture of Multifunctional MPS Particles, Using MPS and Ammonia:

MPS and a 28% by weight aqueous ammonia solution are mixed with a functional material, and then the solution is stirred while the temperature of the solution is kept at a temperature of 80 to 100° C., preferably 95±5° C. for 1 to 12 hours, preferably 7±5 hours. In this way, the reactive components are allowed to react with each other to produce multifunctional MPS particles. The produced multifunctional MPS particles are collected in the form of pellets by high-speed centrifugation. The pellets are washed by centrifugation totally 4 to 8 times, using a 70% solution of ethanol in water, and distilled water alternately. The collected pellets (multifunctional MPS particles) are dispersed with a high-speed homogenizer, or by ultrasonic treatment or the like, and then supplied for use. The particle diameter of the multifunctional MPS particles can be adjusted from nano-sizes to micron-sizes by quantity variation of the concentration of MPS used for the production. For example, the addition amount of MPS to (a constant amount of) the 28% by weight aqueous ammonia solution is adjusted to yield a desired particle diameter, so that the quantity variation can be appropriately attained.

(b) Production of Gold Colloid Coated with an MPS Layer and Containing a Labeling Molecule:

A substance wherein a material reactive with a thiol group, for example, a maleimide compound is bonded to a labeling molecule, for example, rhodamine is allowed to react with the thio group of MPS, thereby preparing an MPS-labeling molecule conjugate in advance. Next, the conjugate, gold colloid, MPS and an aqueous ammonia solution are mixed with one another, or the coupled body, MPS, and an ammonia solution in water are mixed with each other, and then the mixture is stirred while the temperature thereof is kept in the same manner as in the item (a). In this way, a labeling molecule-containing gold colloid coated with an MPS layer is produced. One or more species of the labeling molecule may be incorporated. The silica compound to be used is not limited to MPS, and some other silica compounds may also be used to prepare a different silica compound-labeling molecule conjugate. The particle diameter can be adjusted by the concentration of MPS as described above. The produced gold colloid coated with the MPS layer is collected, washed, and dispersed, and subsequently the colloid is supplied for use. Specific examples thereof will be described in Example 1, which will be given later.

(c) Production of a magnetic material or quantum dot coated with an MPS layer and containing a labeling molecule:

A substance wherein MPS is bonded to a 28% by weight aqueous ammonia solution and a labeling molecule, for example, rhodamine is mixed with a magnetic material or a quantum dot, and then the mixture is stirred while the temperature thereof is kept in the same manner as in the item (a). In this way, magnetic body- or quantum dot-containing multifunctional MPS particles are produced. Specific examples thereof will be described in Example 13 and Example 19, which will be given later.

Next, the usage of the nanofunctional silica particles of the present invention will be described. The nanofunctional silica particles of the invention are used for medicine or bioresearch, such as imaging, assay, diagnosis, or treatment. The following will describe the usage when the functional material is rendered a magnetic material, gold colloid, or a quantum dot.

(1) Magnetic Material Coated with an MPS Layer (a) Improvement in Imaging Technique The magnetic material is expected to be used as a borderless probe capable of making a macro evaluation and a histological evaluation through an MRI. The greatest advantage of the probe for fluorescent MRI is that macro- and micro-observations can be made through the probe alone. Thus, it is considered that various spreading effects would be produced.

(b) Development of a Molecular Target Agent

The surface of the probe is labeled with a new antibody, and the resultant is administered into a living body. The body is then observed by means of an MRI, thereby not only checking targeting into a target internal organ, but also detecting targeting into an unexpected internal organ or tissue. Thus, a forecast or avoidance of a side effect can be attained. Since the targeting can be checked at a cellar level, the targeting into a target tissue can be more precisely estimated. Moreover, particles to which various ligands or the like are bonded are administered, so that targeting results can be screened at a high throughput. Thus, it is considered that the development of a molecular target agent would be further accelerated.

(c) Carrier for Drug Delivery

For example, advantages of treatment of a malignant tumor with the nanofunctional silica particles are as follows: 1) a tumor tissue selecting effect that particles having a size of about 10 nm are easily accumulated onto a tumor site (effect of permeability and retention), 2) a tumor cell selecting effect based on functionalization made by a molecule that is bonded specifically to a tumor, such as an antibody, on the surfaces of the nanoparticles, 3) a target evaluating effect based on a signal function of magnetism, fluorescence or the like, and 4) physically and mechanically selecting effect based on a matter that a chemical agent is incorporated into the particles or the surfaces thereof and then the chemical agent is activated or released by a light ray, heat induced by a magnetic field, or the like. It is considered that these four effects would make it possible to develop an innovational medical care.

(2) Gold Colloid Coated with an MPS Layer

The colloid is expected to be used as a local plasmon resonance probe. According to the present invention, the surface layer modification capability of the gold colloid surface is drastically improved, so that a new assay design using a local plasmon resonance is expected to be constructed.

(3) Quantum dot coated with an MPS layer Expected is the development of a quantum dot for taking high-speed moving images, a low toxin/non toxin quantum dot, a size controlling quantum dot, a fluorescent two quantum dot, and others. By incorporating a fluorescent colorant into the organosilica coat layer, the particles are turned to particles about which the blinking of a quantum dot that has been widely used in recent years is improved, so that a biological phenomenon is observed in more detail. Moreover, the toxicity of the dot is lowered so that safety is given to users. Additionally, the dot can be administered to a living body. Thus, it is considered that the dot would contribute to fluorescent imaging technique.

EXAMPLES

Hereinafter, the constitution and advantages of this invention will be specifically described by way of examples. However, this invention is not limited to only these examples.

Example 1

100 nm gold colloid coated with a 20 nm or less MPS layer

To 90 µL of a 100 nm gold colloid (manufactured by Tanaka Kikinzoku Kogyo K.K.) were each added 100 µL of MPS diluted 500 times and 810 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 20 nm or less MPS layer coat was recognized. The control ratio of the thicknesses of the shells was about 15%.

Example 2

100 nm Gold Colloid Coated with a 10 nm or Less MPS Layer

To 85 µL of a 100 nm gold colloid (manufactured by Tanaka Kikinzoku Kogyo K.K.) were each added 50 µL of MPS diluted 500 times and 865 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 10 nm or less MPS layer coat was recognized. The control ratio of the thicknesses of the shells was about 30%.

Example 3

250 nm Gold Colloid Coated with a 30 nm or Less MPS Layer

To 500 µL of a 250 nm gold colloid (manufactured by BB International) were each added 100 µL of MPS diluted 500 times and 450 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 30 nm or less MPS layer coat was recognized. The control ratio of the thicknesses of the shells was about 16.

Example 4

40 nm Gold Colloid Coated with a 20 nm or Less MPS Layer Containing a Fluorescent Colorant (Rhodamine)

Rhodamine Red TM C2 maleimide (about 5 mg) as a maleimide compound was dissolved in 73.5 µL of a DMSO solution. Thereto was then added (3-mercaptopropyl)-trimethoxysilane having a thiol group, so as to make the mole number of the silane equal to that of Rhodamine Red TM C2 maleimide, and the components were mixed with one another. A tube mixer was used to stir the solution in a light-shaded environment for 2 hours to allow the reactive components to react with one another to prepare a silica compound containing the rhodamine (labeling molecule).

To 400 µL of a 100 nm gold colloid (manufactured by Tanaka Kikinzoku Kogyo K.K.) were each added 100 µL of MPS diluted 500 times, 500 µL of a 28% by weight aqueous ammonia solution, and 100 mM of MPS-rhodamine, and the components were mixed with one another. The reactive components therein were then allowed to react with one another at 100° C. for 4 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 20 nm or less MPS layer coat was recognized. Fluorescence from the rhodamine was able to be recognized with a fluorescence microscope. The control ratio of the thicknesses of the shells was about 17.

Example 5

Labeling of Cells by a Gold Colloid Coated with an MPS Layer Containing a Fluorescent Colorant (Rhodamine)

The particles prepared in Example 4 were administered into a mouse intraperitoneally. The next day, cells in the peritoneal cavity were collected, fixed with 5% paraformaldehyde, and then observed with a fluorescence microscope. According to the fluorescence observation (the right in FIG. 5), cells labeled with the particles and having fluorescence from the rhodamine were able to be recognized. The left in FIG. 5 shows an observation result in a bright visual field, and the middle region in FIG. 5 shows a merged result.

Example 6

Detection of a Protein by Local Plasmon Resonance of a Gold Colloid Coated with an MPS Layer A 100 nm gold colloid coated with a 10 nm or less MPS layer, which was produced by the same method as in Example 2, was used to investigate the detection of a protein by local plasmon resonance. To 900 µL (A1) of a solution of the 100 nm gold colloid coated with an MPS layer were added 9 µL (A2) of a 100 µg/mL anti-glutathione-S-transferase antibody solution and 9 µL (A3) thereof. Thereafter, the absorption of the solution was evaluated (the left in FIG. 6). Considering an effect of the dilution based on the addition of the antibody solution, a correction was made at 400 nm (the left in FIG. 6). A change in the absorption based on the local plasmon resonance was able to be recognized.

Example 7

40 nm Gold Colloid Coated with a 20 nm or More MPS Layer

To 200 µL of a 40 nm gold colloid (manufactured by Tanaka Kikinzoku Kogyo K.K.) were each added 50 µL of MPS diluted 500 times and 250 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 20 nm or more MPS layer coat was recognized. The control ratio of the thicknesses of the shells was about 12.

Example 8

40 nm Gold Colloid Coated with a 20 nm or More TcPS Layer

To 200 µL of a 40 nm gold colloid (manufactured by Tanaka Kikinzoku Kogyo K.K.) were each added 50 µL of (3-thiocyanatopropyl)triethoxysilane (TcPS) diluted 77 times and 250 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 20 nm or more TcPS coat layer was recognized. The control ratio of the thicknesses of the shells was about 20%.

Example 9

40 nm Gold Colloid Coated with a 20 nm or Less TcPS Layer

To 200 µL of a 40 nm gold colloid (manufactured by Tanaka Kikinzoku Kogyo K.K.) were each added 25 µL of (3-thiocyanatopropyl)triethoxysilane (TcPS) diluted 385 times and 275 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 20 nm or more TcPS coat layer was recognized. The control ratio of the thicknesses of the shells was about 6%.

Example 10

40 nm Gold Colloid Coated with a 5 nm or Less TcPS Layer

To 200 µL of a 40 nm gold colloid (manufactured by Tanaka Kikinzoku Kogyo K.K.) were each added 5 µL of (3-thiocyanatopropyl)triethoxysilane (TcPS) diluted 385 times and 295 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 5 nm or more TcPS coat layer was recognized.

Example 11

40 nm Gold Colloid Coated with a 5 nm or Less EpoPS Layer

To 200 µL of a 40 nm gold colloid (manufactured by Tanaka Kikinzoku Kogyo K.K.) were each added 25 µL of 2-(3,4-epoxycyclohexyl)-ethyltrimethoxysilane (EpoPS) diluted 80 times and 275 µL of a 28% by weight aqueous ammonia solution, and the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a 5 nm or more EpoPS coat layer was recognized.

Example 12

Quantum Dot Coated with an MPS Layer

To 3 µL of a Qdot 605 crystal (manufactured by Quantum dot Corporation, 4 µM) were each added 50 µL (a) or 100 µL (b) of MPS diluted 100 times and 947 µL (a) or 897 µL (b) of a 28% by weight aqueous ammonia solution, and then the components were mixed with one another. The reactive components were then allowed to react with one another at 100° C. for 3 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a quantum dot coated with an MPS layer was recognized (the left in FIG. 12 is about (a) and the right in FIG. 12 is about (b)). The control ratio of the sizes of the particles was about 36%.

Example 13

Quantum Dot Coated with an MPS Layer Containing Rhodamine

To 3 µL of a Qdot 605 crystal (manufactured by Quantum dot Corporation, 4 µM) were each added 100 µL of MPS diluted 500 times, 896 µL of a 28% by weight aqueous ammonia solution and 1 µL of 100 mM MPS-rhodamine, and then the components were mixed with one another. The reactive components were then allowed to react with one another at 100° C. for 3 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a quantum dot coated with an MPS layer was recognized (the upper in FIG. 13). Furthermore, a change in the fluorescent intensity of one of the particles was estimated with a fluorescence microscope. In the graph of the lower in FIG. 13, a red line shows the fluorescent intensity of the quantum dot coated with an MPS layer containing rhodamine, and a black broken line shows that of an untreated quantum dot. The quantum dot coated with an MPS layer containing rhodamine was high in intensity and stable so that fluorescence giving no blinking lasted while the untreated quantum dot gave intensely changed fluorescent intensity so that no fluorescence was able to be observed when the intensity lowered (a photo blinking phenomenon). The control ratio of the sizes of the particles was about 21%.

Example 14

Quantum Dot Coated with an MPS Layer, the Surface Layer of which was Modified with a Fluorescent Colorant To 20 µL of a solution containing the quantum dot produced by the method in Example 12, which was coated with an MPS layer, were each added 75 µL of distilled water, and 20 µL of 10 mM fluorescein-5-maleimide (A) or 10 mM DY-635 maleimide (B), and the components were mixed with one another. The reactive components were then allowed to react with one another at 100° C. for 3 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with a fluorescence microscope. Images a to d of the lower in FIG. 14 each show a result of the dot the surface layer of which was modified with the fluorescein (A), and images e to h in FIG. 14 each show a result of the dot the surface layer of which was modified with the DY-635 (B). In each of the images, fluorescence from the Qdot 605 was able to be recognized. Furthermore, fluorescence from the fluorescein was able to be observed in the case (A), and fluorescence from the DY-635 was able to be observed in the case (B). The image d was a result wherein the images a and b were merged, and the image h was a result wherein the images e and g were merged, respectively.

It is understood from these results that the following conjugates can each be bonded directly to the surfaces of the particles: a conjugate composed of maleimide, and a fluorescent colorant such as fluorescein or rhodamine; a conjugate composed of maleimide, and a protein such as streptoamidine, or HRP (horseradish roots peroxidase); and a conjugate composed of maleimide, and a functional material such as biotin, or polyethylene glycol.

Example 15

Modification of a Surface Layer of a Quantum Dot Coated with an MPS Layer with a Protein Into 10 µL of a solution containing the quantum dot produced by the method in Example 12, which was coated with an MPS layer, was mixed with 10 of 10 µg/mL green fluorescent protein (GFP) solution. The reactive components were then allowed to react with one another for several minutes. Next, the reaction finished liquid was subjected to a high-speed centrifugal separator (at 20,000×g for 30 minutes). Pellets thereof were then collected. The resultant pellets were repeatedly washed with physiological saline three times. Next, the washed pellets were stirred in an ultrasonic crusher, and then sampled to be observed with a fluorescence microscope. About the particles, fluorescence (a) from the Qdot and fluorescence (b) from GFP were able to be observed. An image c in FIG. 15 is a merged image of images a and b.

Example 16

Labeling of Cells with a Quantum Dot Coated with an MPS Layer

The particles prepared in Example 13 were administered into a mouse intraperitoneally. The next day, cells in the peritoneal cavity were collected, fixed with 5% paraformaldehyde, and then observed with a fluorescence microscope. According to the fluorescence observation (the right in FIG. 16), cells labeled with the particles and having fluorescence from the rhodamine were able to be recognized. The left in FIG. 16 shows an observation result in a bright visual field, and the middle region in FIG. 16 shows a merged result.

Example 17

Quantum Dot Coated with a TcPS Layer

To 3 μL of a Qdot 605 crystal (manufactured by Quantum dot Corporation, 3 μM) were each added 100 μL of TcPS diluted 385 times and 897 μL of a 28% by weight aqueous ammonia solution, and then the components were mixed with one another. The reactive components were then allowed to react with one another at 100° C. for 4 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a quantum dot coated with an MPS layer was recognized. The control ratio of the sizes of the particles was about 25%.

Example 18

Magnetic Material Coated with an MPS Layer

To 2 μL of 10 nm magnetic particles (manufactured by Ferrotec Corporation) diluted 100 times were each added 100 μL of MPS diluted 500 times, 690 μL of a 28% by weight aqueous ammonia solution and 200 μL of 2-propanol, and then the components were mixed with one another. The reactive components were then allowed to react with one another at 100° C. for 3 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, an MPS layer coat was recognized (the upper in FIG. 18). In a case where the volume of the 28% by weight aqueous ammonia solution and that of 2-propanol were changed to 498 μL and 400 μL, respectively (the lower left in FIG. 18), and changed to 398 μL and 500 μL, respectively (the lower right in FIG. 18), a change in the thickness of the MPS layer coat was recognized. The control ratio of the sizes of the particles was about 13%.

Example 19

Magnetic Material Coated with an MPS Layer Containing a Fluorescent Colorant To 50 μL of 10 nm magnetic particles (manufactured by Ferrotec Corporation) diluted 100 times were each added 100 μL of MPS diluted 500 times, 650 μL of a 28% by weight aqueous ammonia solution, 200 μL of 1,2-propanol and 1 μL of 100 mM MPS-rhodamine, and then the components were mixed with one another. The reactive components were then allowed to react with one another at 100° C. for 4 hours. Next, the reaction finished liquid was subjected to a high-speed centrifugal separator (at 20,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, an MPS layer coat was recognized (the right in FIG. 19). Moreover, fluorescence from the rhodamine was recognized in (the layer of) the particles with a fluorescence microscope (the left in FIG. 19).

Example 20

Labeling of Cells by a Magnetic Material Coated with an MPS Coat Containing a Fluorescent Colorant The particles prepared in Example 19 were administered into a mouse intraperitoneally. The next day, cells in the peritoneal cavity were collected, fixed with 5% paraformaldehyde, and then observed with a fluorescence microscope. According to the fluorescence observation (the right in FIG. 20), cells labeled with the particles and having fluorescence from the rhodamine were able to be recognized. The left in FIG. 20 shows an observation result in a bright visual field, and the middle region in FIG. 20 shows a merged result.

Example 21

Magnetic Material Coated with a TcPS Layer

To 10 μL of 10 nm magnetic particles (manufactured by Ferrotec Corporation) diluted 100 times were each added 100 μL of TcPS diluted 364 times, and 890 μL of a 28% by weight aqueous ammonia solution, and then the components were mixed with one another. The reactive components were then allowed to react with one another at 100° C. for 3 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, an MPS layer coat was recognized. The control ratio of the sizes of the particles was about 13%.

Example 22

Colon Bacilli Coated with an MPS Layer

Colon bacilli JM 109 cultivated for one night were fixed with a 25% glutaraldehyde solution, and the resultant was washed. Thereafter, to 100 μL of the fixed colon *bacillus* liquid were each added 100 μL of MPS diluted 50 times, and 800 μL of a 28% by weight aqueous ammonia solution, and the components were mixed with one another. The reactive components were then allowed to react with one another at 100° C. for 4 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. The left in the figure shows colon bacilli not subjected to coating treatment, and the right in the figure shows colon bacilli subjected to the coating treatment. In the treated bacteria, a change was able to be recognized in the size surface structure of the colon bacilli, and an MPS layer coat was recognized.

Example 23

Modification of a Surface Layer of Colon Bacilli Coated with an MPS Layer with a Protein Colon bacilli JM 109 cultivated for one night were fixed with a 4% paraformaldehyde solution, and the resultant was washed. Thereafter, to 100 μL of the fixed colon *bacillus* liquid were each added 100 μL of MPS diluted 50 times, and 800 μL of a 28% by weight aqueous ammonia solution, and the components were mixed with one another. The reactive components were then allowed to react with one another at 100° C. for 4 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher. Into 5 μL of the colon *bacillus* solution was mixed with a 250 μg/mL green fluorescein protein (GFP) solution, and the resultant was observed with a fluorescence microscope. The upper in FIG. 23 shows colon bacilli not subjected to coating treatment, and the lower in the figure shows colon bacilli subjected to the coating treatment. In the colon bacilli subjected to the coating treatment, fluorescence based on the adhesion of GFP was able to be recognized.

Example 24

Production of Liquid Core Organosilica Shells

The following were mixed with one another: 19 μL of MPS diluted 32 times, 27.7 μL of (3-thiocyanatopropyl)triethoxysilane (TcPS) diluted with 32 times, and 453.3 μL of a 28% by weight aqueous ammonia solution. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, recognized were liquid core organosilica shells, about 300 to 600 nm in diameter, wherein silica shells composed of about 50-100 nm MPS and TcPS were coated with the liquid. The control ratio of the sizes of the particles was about 25%.

Example 25

Production of Liquid Core Organosilica Shells Containing a Fluorescent Colorant

The following were mixed with one another: 19 μL of MPS diluted 32 times, 27.7 μL of (3-thiocyanatopropyl)triethoxysilane (TcPS) diluted with 32 times, 50 μL of a 100 mM fluorescein solution in water, and 403.3 μL of a 28% by weight aqueous ammonia solution. The reactive components were then allowed to react with one another at 100° C. for 4 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, recognized were liquid core organosilica shells wherein silica shells composed of about 60-100 nm MPS and TcPS were coated with the liquid. Furthermore, the sample was observed with a fluorescence microscope, so that significantly stronger fluorescence was observed than in particles produced from MPS only and TcPS only, respectively, by the same method.

Example 26

The following were mixed with one another: 154 of tetraethoxyorthosilicate, 500 μL of ethanol, 125 μL of distilled water, and 50 μL of a 28% by weight aqueous ammonia solution. The reactive components were then allowed to react with one another at room temperature for 2 days to produce inorganosilica TEOS particles.

To 5 μL of the inorganosilica TEOS particles were each added 10 μL of MPS diluted 500 times, 1 μL of 10 mM MPS-rhodamine, and 84 μL of a 28% by weight aqueous ammonia solution, and then the components were mixed with one another. The reactive components were then allowed to react with one another at 100° C. for 3 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, fluorescence was able to be observed from the particles. Thus, it was confirmed that the silica surfaces were coated with the fluorescent colorant-containing organosilica.

Example 27

Quantum Dot Coated with an Organosilica

10 μL of T2-MP EviTags (manufactured by Evident Technologies, Inc.; non-functionalized) was allowed to react with 19 μL of MPS diluted 100 times, 27.7 μL of (3-thiocyanatopropyl)triethoxysilane (TcPS) diluted 100 times, and 443.3 μL of a 28% by weight aqueous ammonia solution at 100° C. for 1.5 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a layer coat made of two organosilica species was recognized.

Example 28

Organosilica Coat-1 of a Magnetic Material

To 4.7 μL of MPS diluted 4 times, 6.9 μL of (3-thiocyanatopropyl)triethoxysilane (TcPS) diluted 4 times, and 388.4 μL of a 28% by weight aqueous ammonia solution was added 100 μL of black iron oxide particles (manufactured by Polyscience, Inc., diameter: about 200 nm) adjusted to 100 mg/mL. The reactive components were then allowed to react with one another at 100° C. for 2 hours. Next, the reaction finished liquid was subjected to a high-speed centrifugal separator (at 10,000×g for 5 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a magnetic material coated with a silica shell layer composed of MPS and TcPS was able to be recognized. According to the upper stage of the lower in the figure, the coated particles were satisfactorily bonded to GFP in the mixing of the particles with a 0.1 mg/mL GFP solution, so that fluorescence was able to be recognized. However, no fluorescence was able to be recognized from uncoated particles in the lower stage.

Example 29

Organosilica Coat-2 of a Magnetic Material

2 μL of 10 nm magnetic particles (manufactured by Ferrotec Corporation) was allowed to react with 19 μL of MPS diluted 100 times, 27.7 μL of (3-thiocyanatopropyl)triethoxysilane (TcPS) diluted 100 times, and 451.3 μL of a 28% by weight aqueous ammonia solution at 100° C. for 1.5 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a silica layer coat was recognized.

Example 30

MRI Evaluation of Organosilica Coated Magnetic Materials

The magnetic material (A) produced in Example 18, which was coated with an MPS layer, and the magnetic material (B) produced in the item <Organosilica coat-2 of a magnetic material>, which was coated with a layer-form MPS and TcPS, were each evaluated by means of a compact MRI for small animals (manufactured by DS Pharma Biomedical Corporation, Ltd.). As a control, liquid core organosilica shells (C) produced in Example-00, which contained no magnetic material and made of MPS and TcPS, were used.

Under T2 emphasis conditions, the magnetic materials each weakened, as a negative imaging agent, signals of water. In the lower in the figures are shown photographed nucleus particles put in respective centrifugal tubes under T2 emphasis conditions. In (C) in the figure, a white positive signal was observed while in each of (A) and (B) in the figure, no positive signal was able to be detected and the signal was in a negative state. It was able to be acknowledged that the organosilica coated magnetic materials each show a negative signal under T2 emphasis conditions of an MRI.

Example 31

Organosilica Coat-1 of Two Functional Material Species: MPS Silica Particles Containing a Quantum Dot and a Magnetic Material To 50 μL, of a Qdot 605 crystal (manufactured by Quantum dot Corporation, 320 μM) and 10 μL of 10 nm magnetic particles (manufactured by Ferrotec Corporation) diluted 100 times were added 100 μL of MPS diluted 500 times and 840 μL of a 28% by weight aqueous ammonia solution, and then the components were mixed with one another. The reactive components were then allowed to react with one another at 100° C. for 3 hours. Next, the reaction finished liquid was subjected to a high-speed centrifugal separator (at 20,000×g for 15 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, hybrid particles of a quantum dot and a magnetic material that were coated with an MPS layer were recognized.

Example 32

Organosilica Coat-2 of Two Functional Material Species: Organosilica Particles Containing a Quantum Dot and a Magnetic Material To 24 of 10 nm magnetic particles (manufactured by Ferrotec Corporation) diluted 20 times were each added 5 μL of 10 μM T2-MP EviTags (manufactured by Evident Technologies, Inc.; non-functionalized), 19 μL of MPS diluted 100 times, 27.7 μL of TcPS diluted 100 times, and 438.3 μL of a 28% by weight aqueous ammonia solution, and then the components were mixed with one another. The reactive components were then allowed to react with one another at 100° C. for 1.5 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Furthermore, the washed pellets were stirred in an ultrasonic crusher, and then sampled to be observed with an electron microscope. As a result, an organosilica layer coat was recognized.

Example 33

Coating with Two Organosilica Species: APS/MPS Coat

To 100 μL of 10 nm magnetic particles (manufactured by Ferrotec Corporation) diluted 100 times were each added 19 μL of MPS diluted 40 times, 22.6 μL of APS diluted 40 times, and 448.4 μL of a 28% by weight aqueous ammonia solution, and then the components were mixed with one another. The reactive components were then allowed to react with one another at 100° C. for 16 hours. Next, the reaction finished liquid was subjected to a high-speed centrifugal separator (at 20,000×g for 30 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, a magnetic material coated with an APS/MPS layer was recognized. Particles made of APS/MPS containing no magnetic particle were also observed.

Example 34

Production of a Magnetic Material Coated with an MPS Layer, Using a Magnetic Material Insoluble in Water To 32 mg of dry magnetic particles (EMG 1500, manufactured by Ferrotec Corporation) were each added 10 μL of MPS, 940 μL of a 28% by weight aqueous ammonia solution and 50 μL of 10 mM Rhodamine B, and then the components were mixed with one another. The reactive components were then allowed to react with one another at 100° C. for 3 hours. Next, the reaction finished liquid was subjected to a high-speed centrifugal separator (at 20,000×g for 10 minutes). Pellets thereof were then collected. The resultant pellets were repeatedly washed by centrifugation totally 6 times, using 70% by volume ethanol and distilled water alternately three times, respectively. Next, the washed pellets were stirred in an ultrasonic crusher, and then sampled to be observed with an electron microscope. As a result, magnetic particles coated with an MPS layer were recognized (FIG. 34). Fluorescence was able to be observed from the particles with a fluorescence microscope (FIG. 35). The coated particles were dispersed in water.

The hydrophobic type magnetic particles were allowed to undergo silica coating reaction, whereby the particles were able to be made hydrophilic. The coated particles were turned to particles high in dispersibility as illustrated in FIG. 36. The particles before the coating (the left in the figure) aggregate to precipitate or rise to the surface of water while the coated particles (the right in the figure) are dispersed.

Through one-stage reaction with only Rhodamine B without using a conjugate of a silica compound and a fluorescent colorant (such as MPS-rhodamine), the colorant is contained in the organic silica coating layer of the particles.

Example 35

Comparison in Surface Modifying Capability Between Gold Colloid Particles Coated with MPS and Conventional Gold Colloid Particles Produced were green fluorescein protein (GFP) solutions having various concentrations (0 to 20 μg/mL, specifically 0, 10 and 20 μg/mL). Into a test tube for a flow cytometer were put 5 μL of each of the GFP solutions and 5 μL of each of particle solutions A to E described below, and then the solutions were sufficiently mixed with each other. Thereafter, (without taking any period especially for reaction), the mixture was diluted with 490 μL of distilled water and then the solution was measured by flow cytometry (FCM-48-3820).

A: a 100 nm gold colloid.
B: a 100 nm gold colloid coated with SiO2.
C: a 100 nm gold colloid coated with SiO2 and then treated with MPS.
D: a 100 nm gold colloid coated with SiO2 and then treated with APS.
E: a 100 nm gold colloid coated with MPS.

It is understood that among these particles, the particles A to D are conventional coated particles, and the surface of which was treated with APS or MPS as a coupling agent while the particles E are particles E coated with MPS, which are one example of the present invention.

The measurement results by the flow cytometry are shown in Tables 2 and 3 describe below, and a graph of the results is shown in FIG. 37. Table 2 shows the measurement results of the individual particles A to E. Table 3 shows results obtained by subtracting, therefrom, results in a case where the concentration was 0 μg/mL in Table 1 as background data. FIG. 37 shows a graph of the data in Table 2. The coated particles (E) showed surface modifying capability about 3-30 times higher than that of other particles when the GFP concentration was 20 μg/mL. From this matter, it is understood that particles wherein a gold colloid is coated directly with MPS are higher in protein bonding efficiency than other coated particles.

TABLE 2

|    | A    | B    | C    | D    | E     |
|----|------|------|------|------|-------|
| 0  | 1.63 | 1.47 | 1.54 | 1.59 | 2.06  |
| 10 | 1.8  | 1.66 | 3.97 | 1.96 | 4.31  |
| 20 | 1.97 | 2.32 | 5.2  | 2.17 | 12.59 |

TABLE 3

|    | A    | B    | C    | D    | E     |
|----|------|------|------|------|-------|
| 0  | 0    | 0    | 0    | 0    | 0     |
| 10 | 0.17 | 0.19 | 2.43 | 0.37 | 2.25  |
| 20 | 0.34 | 0.85 | 3.66 | 0.58 | 10.53 |

Example 36

Surface Functionalization by Use of a Chemically Conjugating Material of Organosilica Coated Particles Used was a chemically conjugating material for bonding a protein more effectively to the surfaces of particle coated with an organosilica, specifically 4-maleimidobutyric acid N-succinimidyl ester, which is a maleimide compound as a coupling agent, to produce an effective result. Specifically, produced were green fluorescein protein (GFP) solutions having various concentrations (0 to 50 μg/mL, specifically 0, 12.5, 25, and 50 μg/mL). Into a test tube for a flow cytometer were put 25 μL of each of the GFP solutions and 5 μL of each of particle solutions A to C described below, and then the solutions were sufficiently mixed with one another. Thereafter, the mixture was diluted with 470 μL of distilled water and then the solution was measured by flow cytometry (in the same way as in Example 35).

A: a 250 nm gold colloid.
B: a 250 nm gold colloid coated with MPS.
C: particles obtained by adding 4-maleimidobutyric acid N-succinimidyl ester to 250 μL of particles wherein a 250 nm gold colloid was coated with MPS so as to give a final concentration of 1 mM, and then allowing the reactive components to react with one another for 1 hour.

4-Maleimidobutyric acid N-succinimidyl ester is one of chemically conjugating materials which can be bonded to an amino group of a protein and a thiol group of MPS-coated particles to bond the protein to the surfaces of the particles. For the present particles, particles having a surface on which the succimide ester was allowed to be held are produced.

The results measured by the flow cytometry are shown in Table 4 described below. A graph thereof is shown in FIG. 38. Table 4 shows the measurement results of the individual particles A to C. The results are results obtained by subtracting, therefrom, results in a case where the concentration was 0 μg/mL as background data. FIG. 38 shows a graph of the data in Table 4. From this matter, it is understood that when 4-maleimidobutyric acid N-succinimidyl ester as a chemically conjugating material is bonded to MPS, the resultant particles are higher in protein bonding efficiency than other particles.

TABLE 4

|  | A | B | C |
|---|---|---|---|
| 0 | 0 | 0 | 0 |
| 12.5 | 0.04 | 1.7 | 3.04 |
| 25 | 0.11 | 1.98 | 3.76 |
| 50 | 1.12 | 5.25 | 7.76 |

These results (in Examples 35 and 36) demonstrate that these examples are excellent surface functionalizing capability of particles themselves, an excellent method for functionalizing particle surfaces, and excellent particles the surfaces of which are functionalized at a high level, and have not been obtained in the prior art by the application of an organosilica coated layer and a coupling agent. Additionally, the particle surfaces obtained by allowing N-succinimidyl 4-maleimidobutyrate to react with a gold colloid coated with an MPS layer make it possible that the surfaces are conjugately bonded to any material having an amino group, such as a protein having an amino group, or amino labeled DNA, by the existence of the succimide ester. Furthermore, when 1,2-bis(maleimido)ethane is allowed to react with particles coated with an MPS layer, the particles are turned to particles having a surface having a maleimide group, so that the particles can be bonded to a protein having a thiol group or some other functional materials. This reaction is not limited to any single-stage reaction, and may be made into a multistage reaction. By a multi-stage reaction of various coupling agents, various particle surfaces can be functionalized.

Example 37

Zeta Potential of Particles Coated with an Organosilica

About various functional particles that were to be cores, a measurement was made on the difference in zeta potential (Z potential difference) between a case where the particle was not subjected to surface modification (coating), and a case where the particle was coated with a silica compound. Table 5 shows, from the left column successively toward the right, the zeta potential of each particle, the zeta potential difference between the particle and its core particle, the absolute value of the zeta potential difference between the particle and the core particle, and explanation of the core particle and the particle that covers this core particle.

TABLE 5

|  | Z potential measurement value | Difference from core particles | Value of difference from core particles | Explanation of particles |
|---|---|---|---|---|
| Qdots-605 | −19.2 |  |  | Quantum dot named Qdots |
| ((Qdots-605)MPS) | −28.16 | −8.96 | 8.96 | Particles wherein Qdots-605 was coated with MPS |
| Au100 nm | −27.82 |  |  | Gold colloid particles named Au 100 nm and having a diameter of 100 nm |
| ((Au100 w)MPS) | −36.51 | 8.69 | 8.69 | Particles wherein Au 100 nm was coated with MPS |
| ((Au100 w)TcPS) | −39.92 | −12.1 | 12.1 | Particles wherein Au 100 nm was coated with TcPS |
| ((Au100 w)EpoPS) | −0.12 | 27.7 | 27.7 | Particles wherein Au 100 nm was coated with EpoPS |
| Au-BB-250 nm | −16.2 |  |  | Gold colloid particles named Au-BB-250 nm and having a diameter of 250 nm |
| ((Au-BB-250 nm)MPS) | −36.37 | 20.17 | 20.17 | Particles wherein Au-BB-250 nm was coated with MPS |
| ((Au-BB-250 nm)MPS)-NHS | −0.87 | 15.33 | 15.33 | Particles obtained by allowing 4-maleimidobutyric acid N-succinimidyl ester to react with particles wherein Au-BB-250 nm was coated with MPS |
| EMG707 | −48.35 |  |  | Magnetic particles named EMG707 and manufactured by Ferrotec Corporation |
| ((EMG707)MPS) | −36.9 | 11.45 | 11.45 | Particles wherein EMG707 was coated with MPS |
| ((EMG1500)RhodamineB/MPS | −57.34 | −8.99 | 8.99 | Particles wherein EMG1500 was coated with MPS and TcPS |
| ((EMG707/Evi583)MPS/TcPS | −40.44 | 7.91 | 7.91 | Particles wherein EMG707 and Evi583 as a quantum dot were coated with MPS and TcPS |

Example 38

Inspection of a Cell Damaging Function by Irradiation with Excited Light Rays: (EMG1500)Rhodamine B/MPS Particles In the present example, RPMI containing 2 mL of 10% FBS was used to collect macrophages from a mouse peritoneal cavity, and the macrophages were cultivated in a 96-well microplate. Thereafter, 10 μL of a cell proliferation reagent (WST-1 manufactured by Roche Diagnostics K.K.) was added to each of the solutions according to the following conditions A to C, and then the macrophages were cultivated for 30 or 90 minutes. The absorption wavelength (440 nm) of the resultant solutions was then measured (reference wavelength: 750 nm).

A: 100 μL of peritoneal macrophages

B: To 100 μL of peritoneal macrophages were added 10 μL of ((EMG1500)Rhodamine B/MPS) particles.

C: To 100 μL of peritoneal macrophages were added 10 μL of ((EMG1500)Rhodamine B/MPS) particles, and then the resultant was irradiated with excited light rays (528-553 nm) under a fluorescence microscope.

The ((EMG1500)Rhodamine B/MPS) particles were particles obtained by incorporating a fluorescent colorant (Rhodamine B) into dry magnetic nanoparticles EMG1500 (manufactured by Ferrotec Corporation), and then coating the resultant particles with MPS.

Table 6 described below shows, in the upper thereof, a case where the macrophages were cultivated on the microplate for 30 minutes, and shows, in the lower thereof, a case where the macrophages were cultivated thereon for 90 minutes. About each of the samples, the absorption wavelength of 450 nm and that of 750 nm were measured, and the absorbances at the respective wavelengths are shown. Table 7 shows results each obtained by subtracting the measured value of the absorbance at the absorption wavelength of 750 nm as background data from the measured value of the absorbance at the absorption wavelength of 440 nm. FIG. 39 is a chart obtained by graphing, from the results in Table 7, the absorbance in the case of 30-minute cultivation and that in the case of 90-minute cultivation. The left therein shows the results in the case of 30-minute cultivation, and the right therein shows those in the case of 90-minute cultivation. The value of each of the absorbances referred to herein is in proportion to the proliferation activity of cells, and is in inverse proportion to the degree that cells are damaged. That is, the height of a bar graph of FIG. 39 is in proportion to the proliferation activity of the microphages. A relative fall in the bar graph demonstrates that the microphage cells are damaged so that the proliferation thereof is lowered.

As understood from these results, the microphages proliferated'under the condition B are reduced under the condition C where the microphages are irradiated with excited light rays. That is, it is recognized that the proliferation activity of the cells is lowered by the irradiation with excited light rays. It is considered that this would be because the cells are damaged by the effect of active oxygen that is generated by the particles. Accordingly, it can be said that the present particles have not only an imaging function but also a cell damaging function under conditions that the particles are irradiated with excited light rays.

FIG. 40 shows a change in the form of the cells (microphages) irradiated with excited light rays (528-553 nm) under a fluorescence microscope (the condition C). At the start of the irradiation (at 0 sec), fluorescence can be observed from the particles in the cells. However, after 100 sec, the fluorescence is lost, and then a change in the form of the cells and a result of a break thereof are observed.

The particles in present Example 38 are expected to be applied to magnetic fluid hyperthermia, which is a treatment method to which attention has been paid in recent years. This treatment method is a method of accumulating magnetic particles in a tumor site in a living body, applying a magnetic field to the body to generate heat in the magnetic material, thereby killing and wounding the tumor cells, which are high in sensitivity to heat. When the present particles are used in this treatment method, the killing and wounding effect can be made better than killing and wounding of tumor cells by heat in the prior art. This is because the particles have a cell damaging function based on irradiation with light.

TABLE 6

|  |  | 0 | 440 (wavelength) | 0 | 750 (wavelength) | 0 |
|---|---|---|---|---|---|---|
| 30 min | A |  | 440 | 0.141 | 750 | 0.004 |
|  | B |  | 440 | 0.166 | 750 | 0.01 |
|  | C |  | 440 | 0.12 | 750 | 0.009 |
| 90 min | D |  | 440 | 0.289 | 750 | 0.009 |
|  | E |  | 440 | 0.327 | 750 | 0.012 |
|  | F |  | 440 | 0.23 | 750 | 0.014 |

TABLE 7

|  | 30 min | 90 min |
|---|---|---|
| A | 0.137 | 0.28 |
| B | 0.156 | 0.315 |
| C | 0.111 | 0.216 |

Besides the above-mentioned silica coat, it is considered that other silica coats as described in the following would be allowable: a silica coat made of only one out of various organosilicas, such as 2-(carbomethoxy)ethyltrimethoxysilane, which is a silica compound having a carboxyl group, or a silica coat wherein two or more of the organosilicas are mixed with each other. As the core particles thereof, gadolinium containing particles are also allowable.

Figure 13:
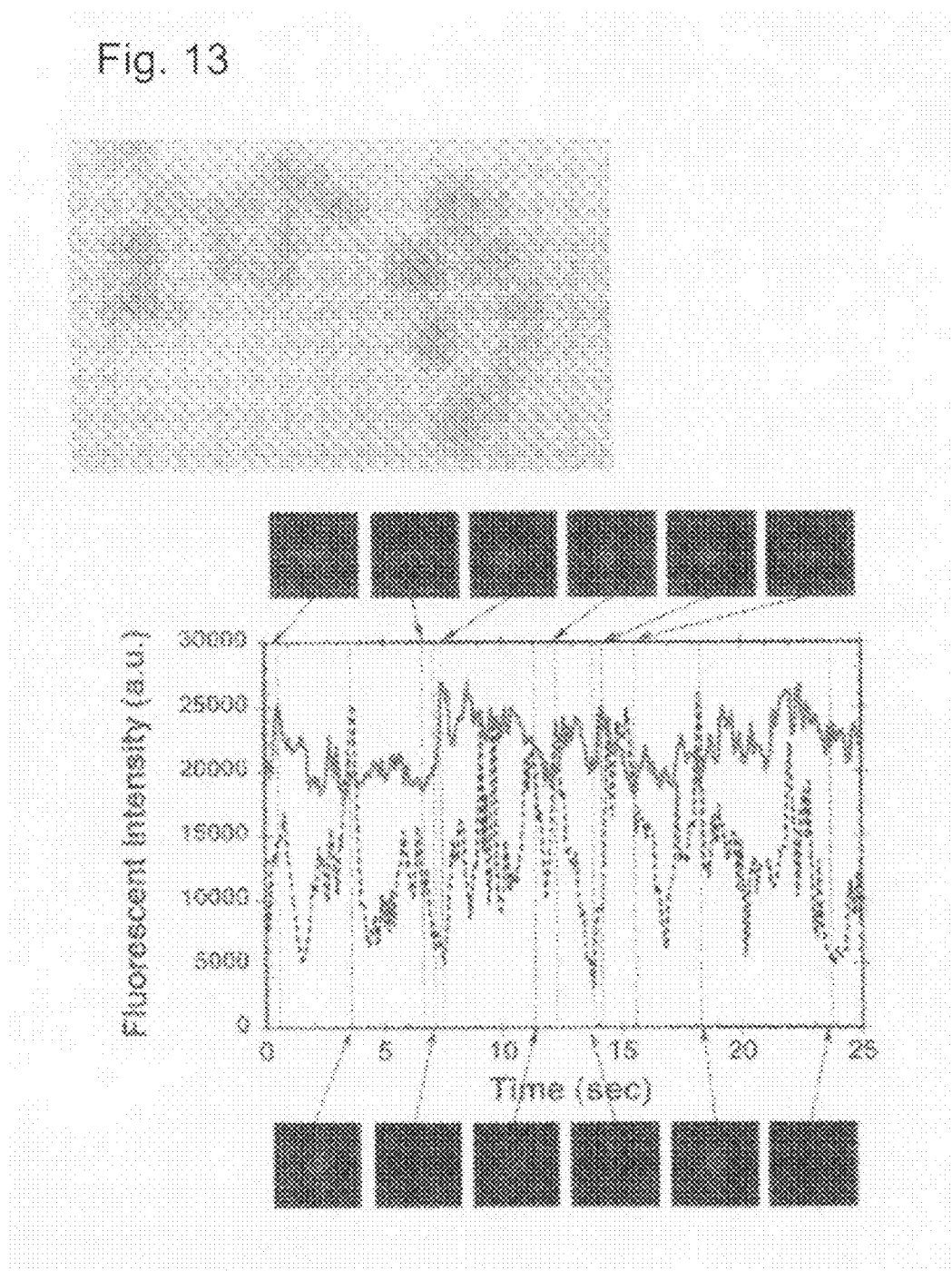

The upper in FIG. 13 is an electron microscopic image of multifunctional MPS layer-form particles containing therein a particle dot and having a fluorescent colorant (rhodamine) (Example 13). The lower in the figure is a graph wherein a change in the fluorescent intensity of one of the particles was estimated with a fluorescence microscope. In the graph of the lower in the figure, a red line shows the fluorescent intensity of the quantum dot coated with an MPS layer containing rhodamine, and a black broken line shows the fluorescent intensity of an untreated quantum dot.

Figure 1:
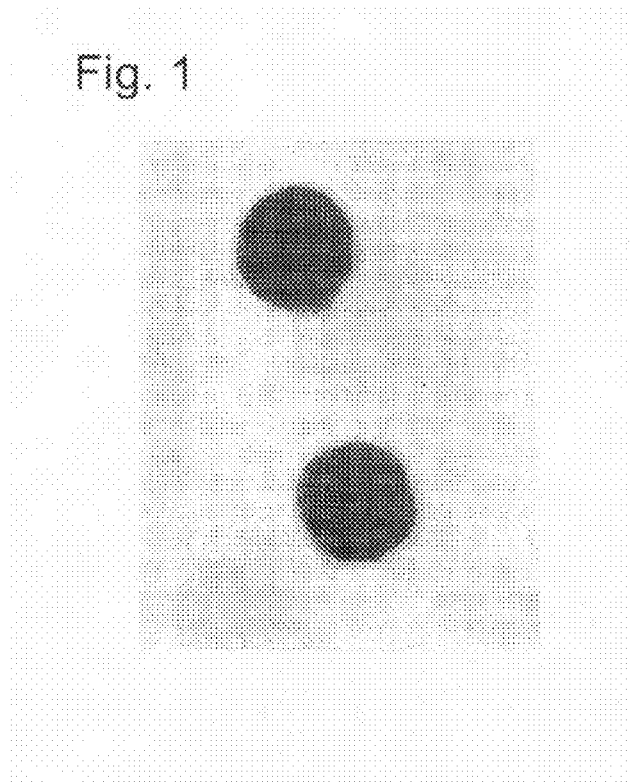
FIG. 1 shows 20 nm or less multifunctional MPS particles containing therein a 100 nm gold colloid (Example 1).
Figure 2:
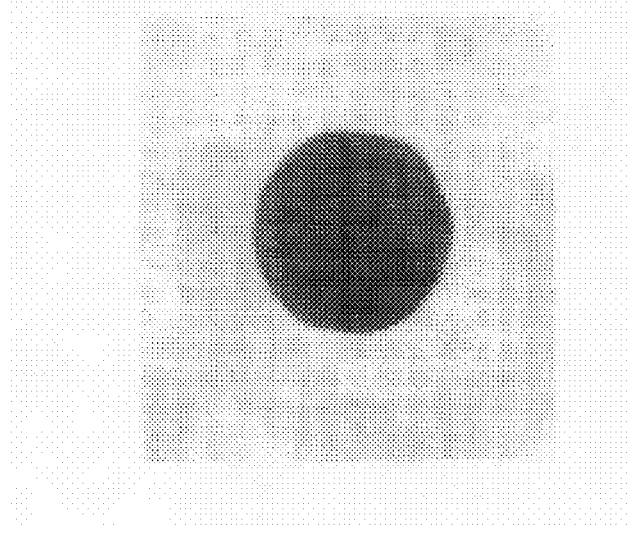
FIG. 2 is an electron microscopic image of 10 nm or less multifunctional MPS layer-form particles containing therein a 100 nm gold colloid (Example 2).
Figure 3:
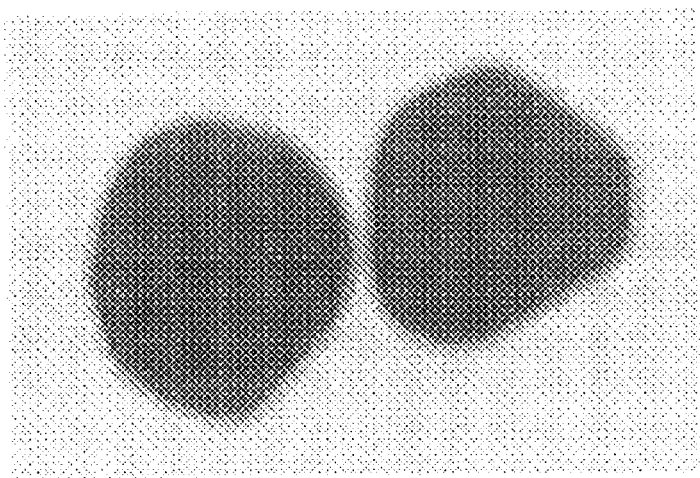
FIG. 3 is an electron microscopic image of 30 nm or less multifunctional MPS layer-form particles containing therein a 250 nm gold colloid (Example 3).
Figure 4:
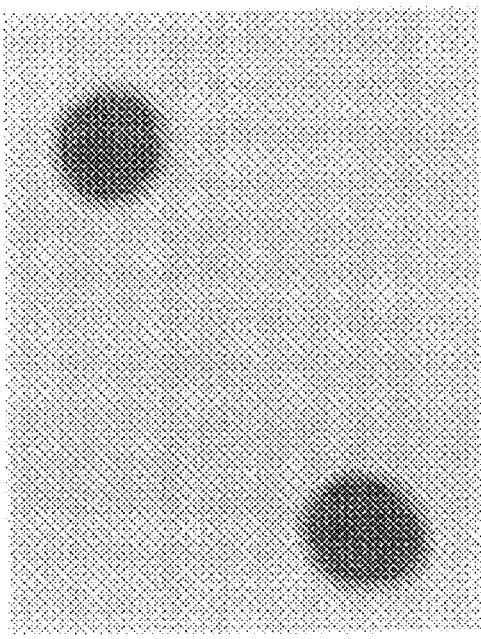
FIG. 4 is an electron microscopic image of 20 nm or less multifunctional MPS layer-form particles containing therein a 40 nm gold colloid and further having a fluorescent colorant (rhodamine) (Example 4).
Figure 5:
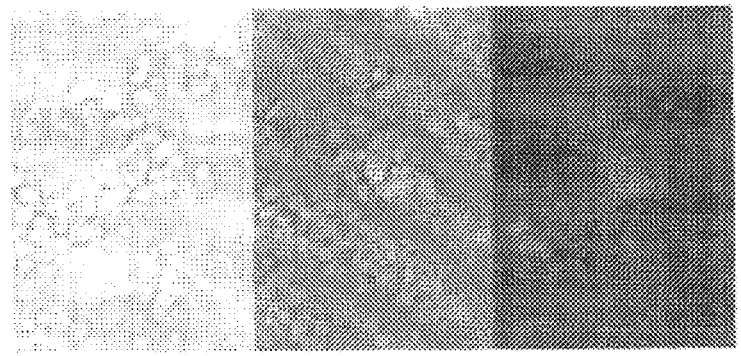
FIG. 5 is a fluorescence microscopic image of cells in a mouse peritoneal cavity that were collected after particles produced in Example 4 were administered intraperitoneally (the right in the figure) (Example 5). The left in the figure shows an observation result in a bright visual field, and the middle region therein shows a merged result.
Figure 6:
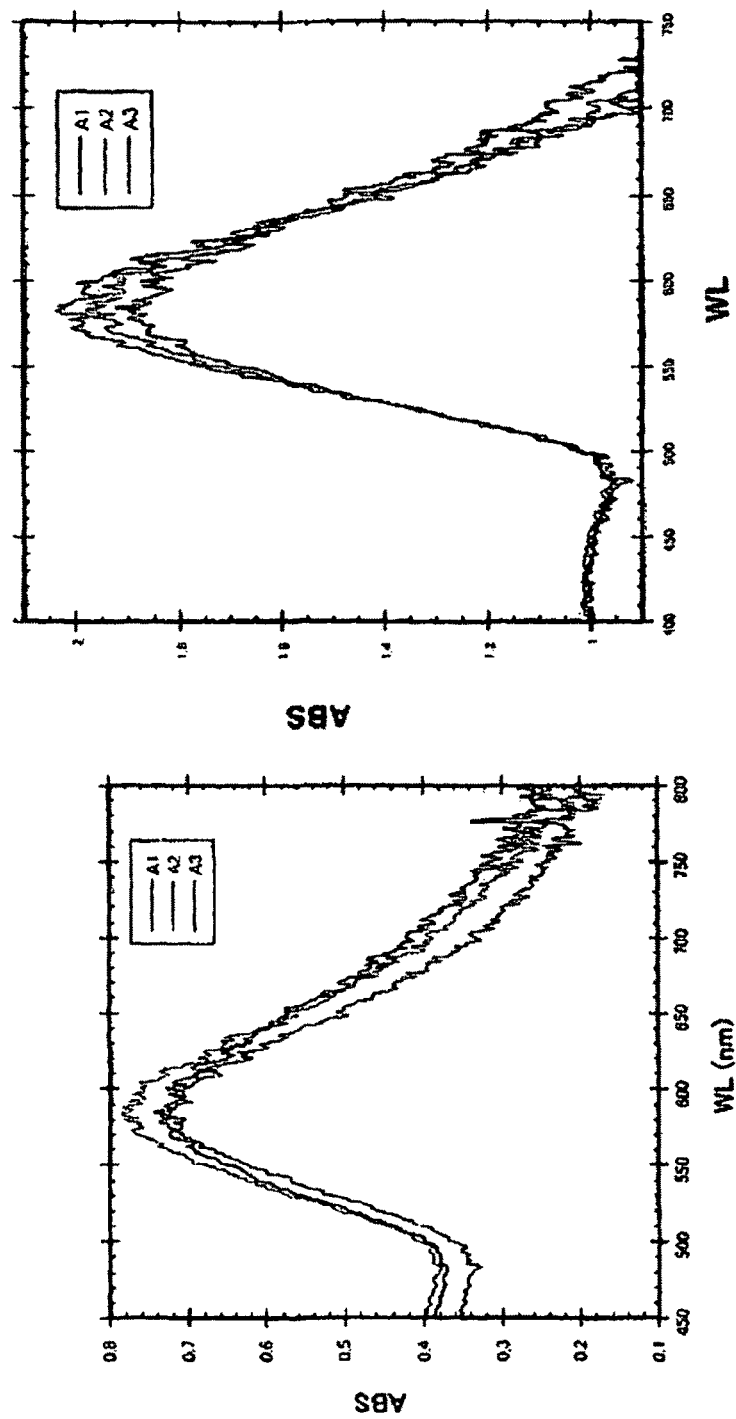
FIG. 6 shows graphs each showing results of a detection of a protein by local plasmon resonance, using particles produced in Example 2 (Example 6). The left in the figure is a graph obtained in a case where to 900 μL (A1) of a solution of a 100 nm gold colloid coated with an MPS layer were added 9 μL (A2) of a 100 μg/mL anti-glutathione-S-transferase antibody solution and 9 μL (A3) thereof, and subsequently the absorption of the solution was estimated. The left in the figure is a graph obtained in a case where a correction was made at 400 nm, considering an effect of the dilution based on the addition of the antibody solution.
Figure 7:
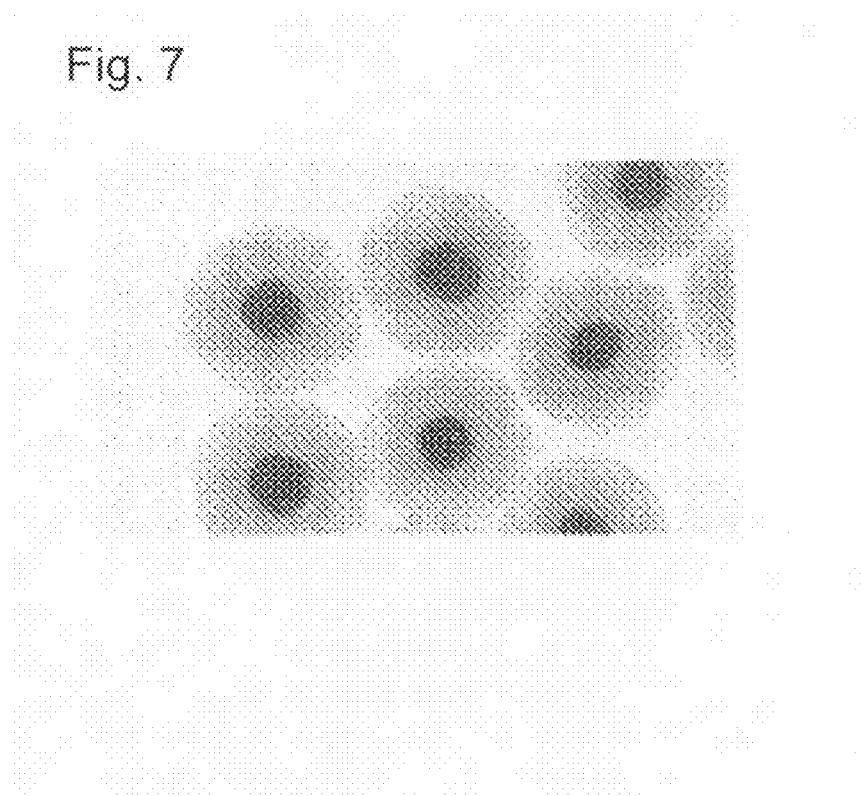
FIG. 7 is an electron microscopic image of 20 nm or more multifunctional MPS layer-form particles containing therein a 40 nm gold colloid (Example 7).
Figure 8:
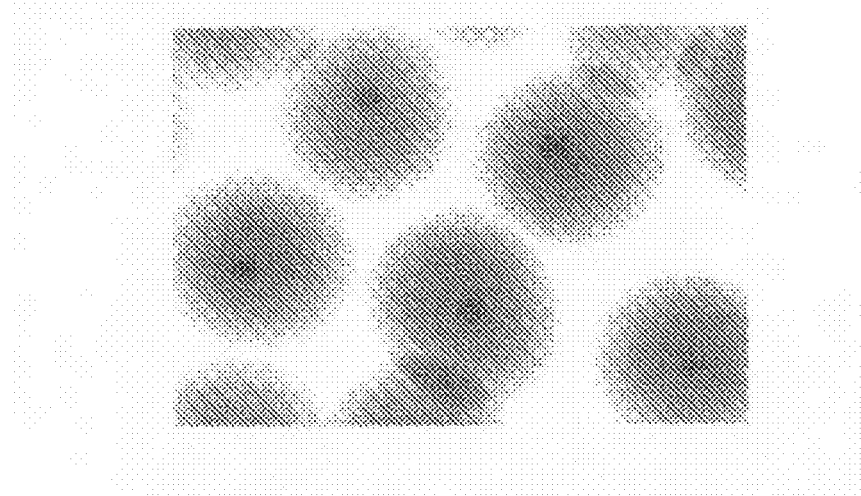
FIG. 8 is an electron microscopic image of 20 nm or more multifunctional TcPS layer-form particles containing therein a 40 nm gold colloid (Example 8).
Figure 9:
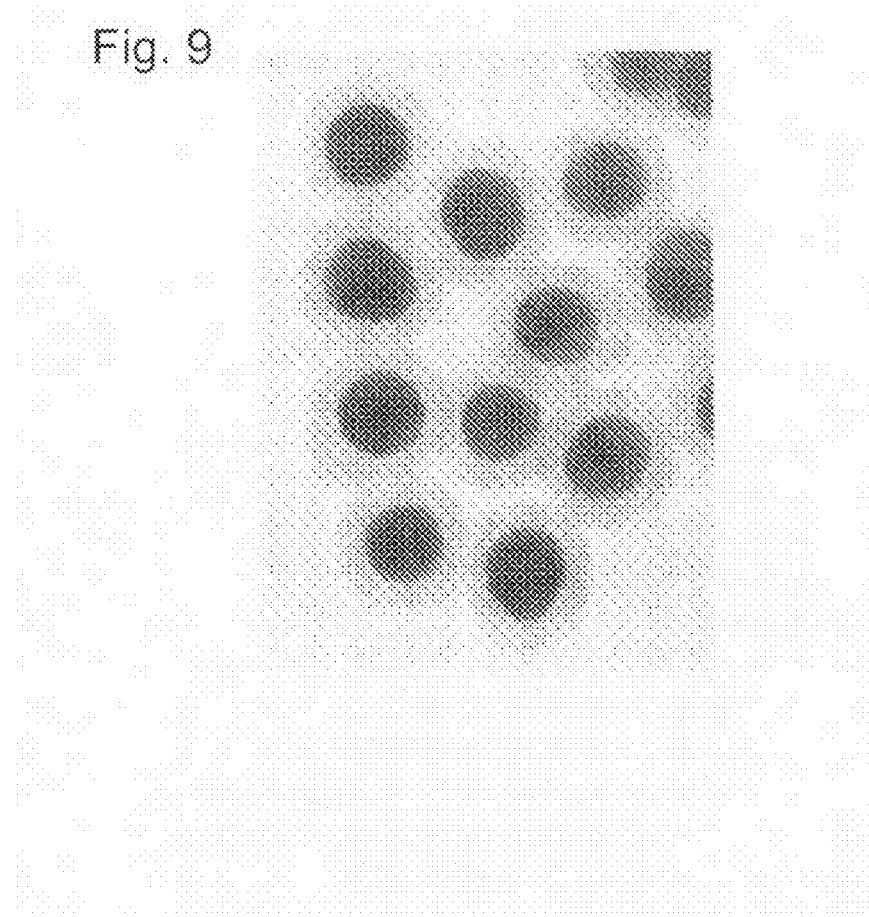
FIG. 9 is an electron microscopic image of 20 nm or less multifunctional TcPS layer-form particles containing therein a 40 nm gold colloid (Example 9).
Figure 10:
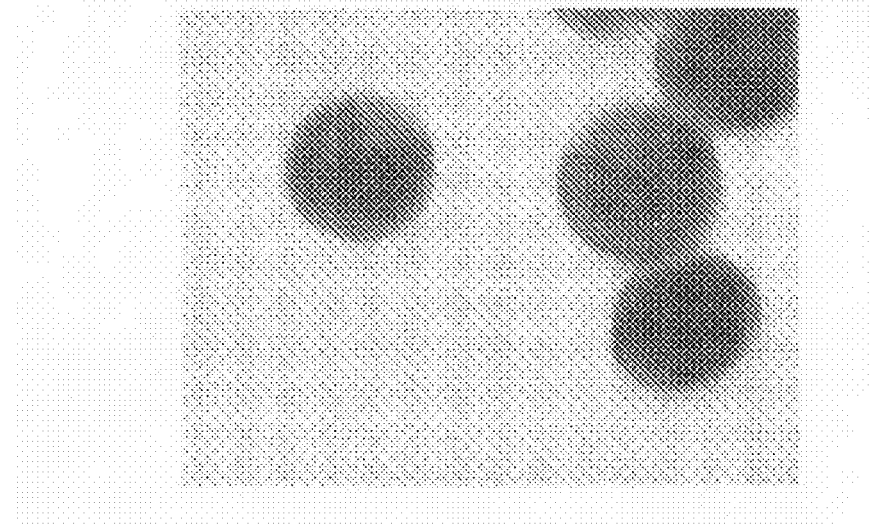
FIG. 10 is an electron microscopic image of 5 nm or less multifunctional TcPS layer-form particles containing therein a 40 nm gold colloid (Example 10).
Figure 11:
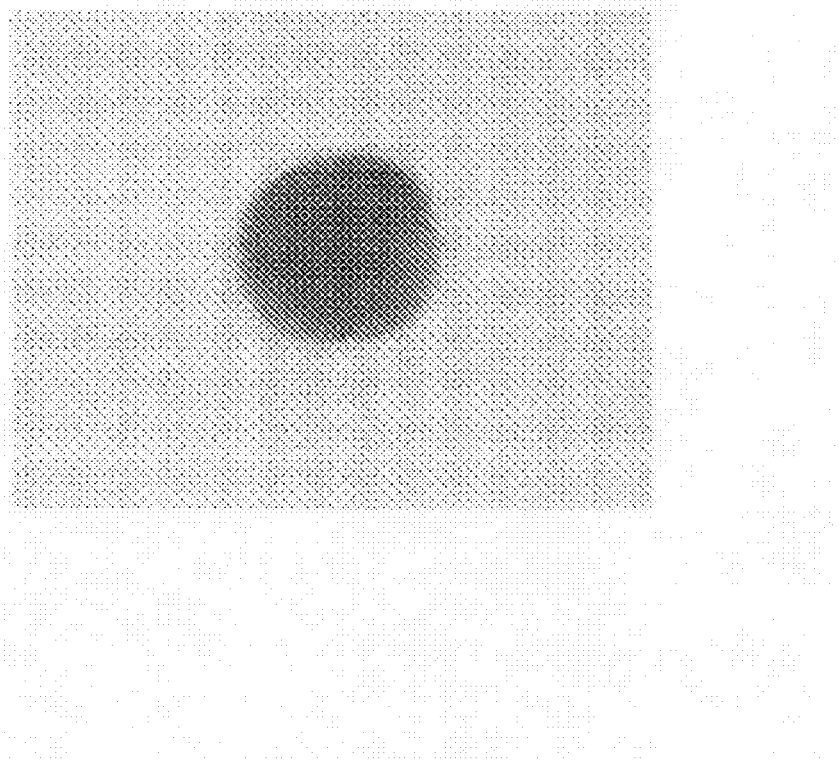
FIG. 11 is an electron microscopic image of 5 nm or less multifunctional EpoPS layer-form particles containing therein a 40 nm gold colloid (Example 11).
Figure 12:
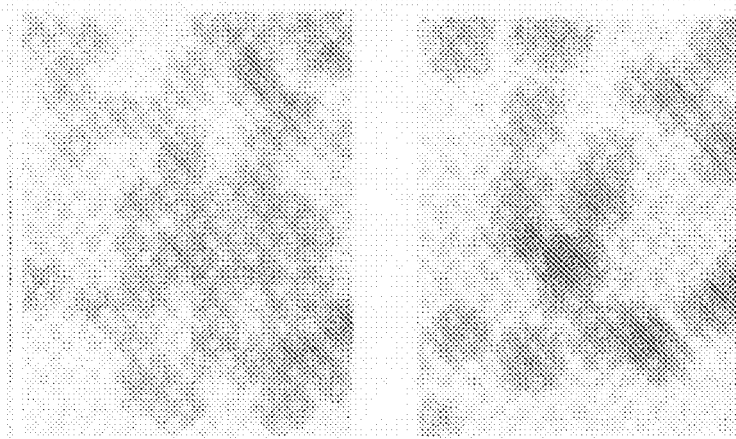
FIG. 12 is an electron microscopic image of multifunctional MPS layer-form particles containing therein a particle dot (Example 12). The left in the figure shows particles produced by use of 50 μL of MPS diluted 100 times, and the right in the figure shows particles produced by use of 100 μL of the same MPS.
Figure 14:
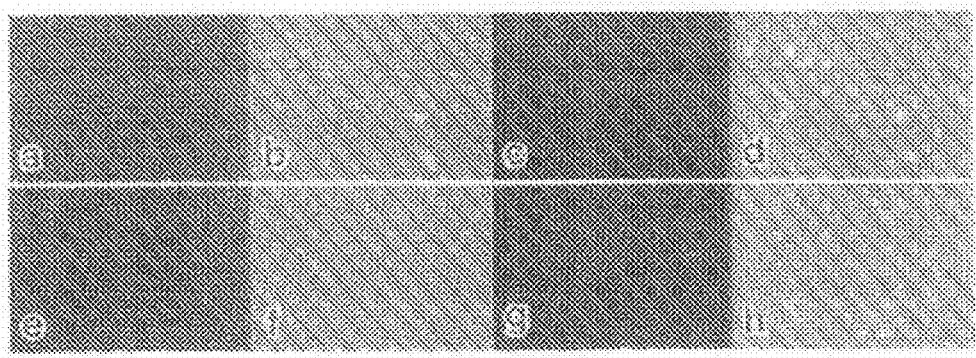

FIG. 14 is a fluorescence microscopic image of multifunctional MPS layer-form particles containing therein a particle dot, wherein the surface layer of the particles produced in FIG. 12 was modified with a fluorescent colorant (Example 14). Images a to d in the lower in the figure each show a result of the particles the surface layer of which was modified with the fluorescein (A), and images e to h in the figure each show a result of the particles the surface layer of which was modified with DY-635 (B). The image d was a result wherein the images a and b were merged, and the image h was a result wherein the images e and g were merged, respectively.

Figure 15:
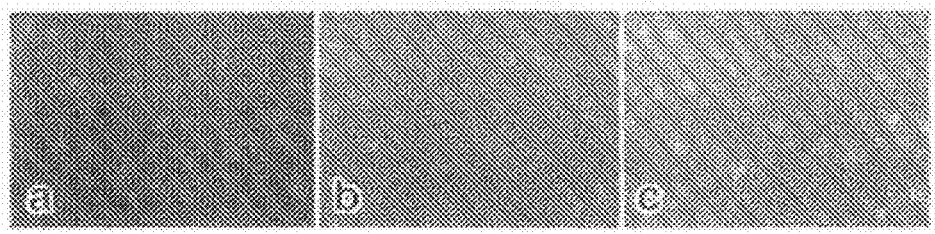

FIG. 15 is a fluorescence microscopic image of multifunctional MPS layer-form particles containing therein a particle dot, wherein the surface layer of the particles produced in Example 12 was modified with a green fluorescent protein (GFP) (Example 15). In the figure, images a, b and c are fluorescence from Qdot, fluorescence from GFP, and a merged image of images a and b, respectively.

Figure 16:
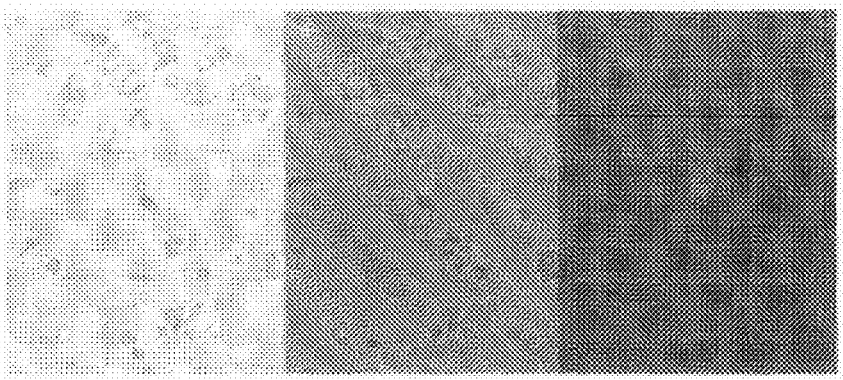

FIG. 16 is a fluorescence microscopic image of cells in a mouse peritoneal cavity that were collected after the particles produced in Example 13 were administered intraperitoneally (the right in the figure) (Example 16). The left in the figure shows an observation result in a bright visual field, and the middle region therein shows a merged result.

Figure 17:
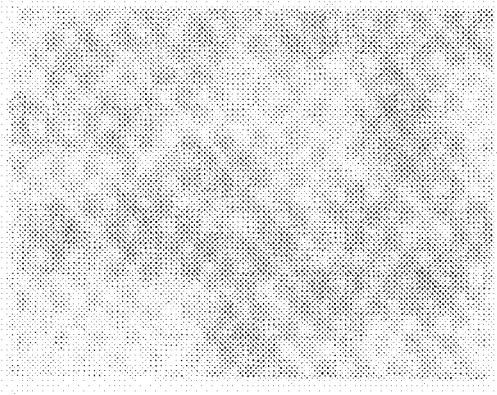

FIG. 17 is an electron microscopic image of multifunctional TcPS layer-form particles containing therein a quantum dot (Example 17).

Figure 18:
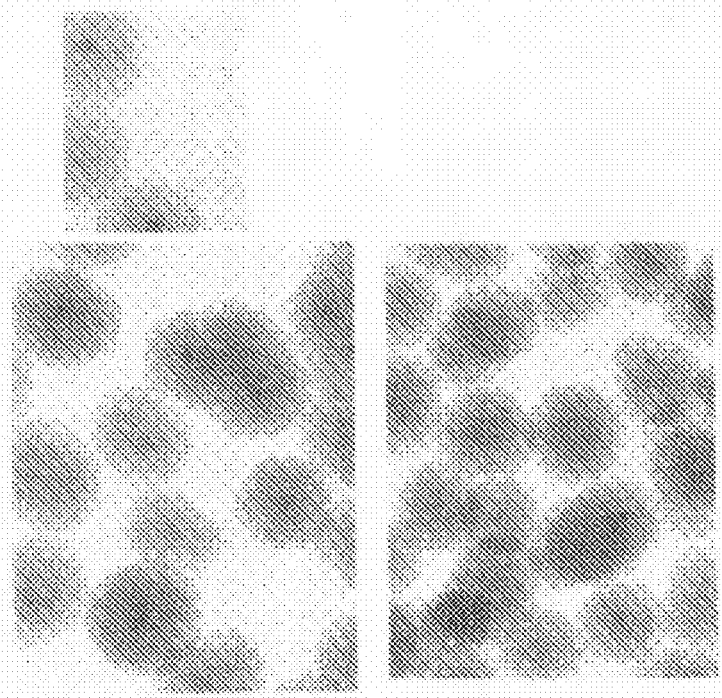

FIG. 18 is an electron microscopic image of multifunctional MPS layer-form particles containing therein a magnetic particle (Example 18). The upper in the figure, the lower left therein, and the lower right therein show in a case where the volume of a 28% by weight aqueous ammonia solution and that of 2-propanol were set to 690 μL and 200 μL, respectively (the upper in the figure), set to 498 μL and 400 μL, respectively (the lower left therein), and set to 398 μL and 500 μL, respectively (the lower right therein), respectively.

Figure 19:
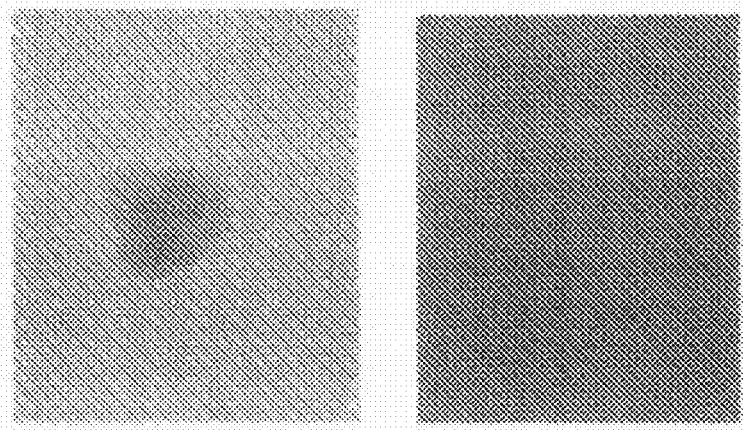

The right in FIG. 19 is an electron microscopic image of multifunctional MPS layer-form particles containing therein a magnetic particle and having a fluorescent colorant (rhodamine). The left in the figure is a view wherein fluorescence from rhodamine was recognized in (the layer of) the particles with a fluorescence microscope (Example 19).

Figure 20:
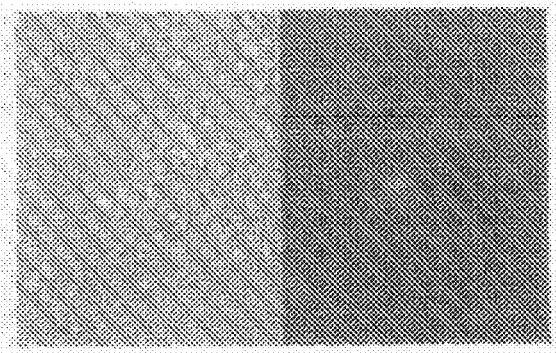

FIG. 20 is a fluorescence microscopic image of cells in a mouse peritoneal cavity that were collected after the particles produced in Example 19 were administered intraperitoneally (the right in the figure) (Example 20). The left in the figure shows an observation result in a bright visual field, and the middle region therein shows a merged result.

Figure 21:
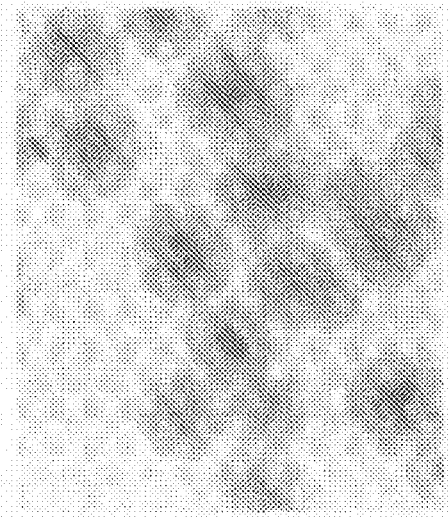

FIG. 21 is an electron microscopic image of multifunctional TcPS layer-form particles containing therein a magnetic particle (Example 21).

Figure 22:
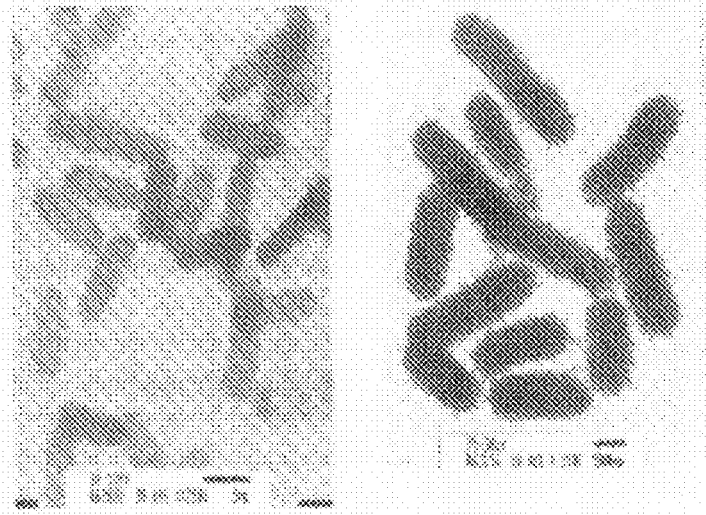

FIG. 22 is an electron microscopic image of colon bacilli JM109 coated with an MPS layer. The left in the figure shows colon bacilli not subjected to any coating treatment, and the right therein shows colon bacilli subjected to the coating treatment (Example 22).

Figure 23:
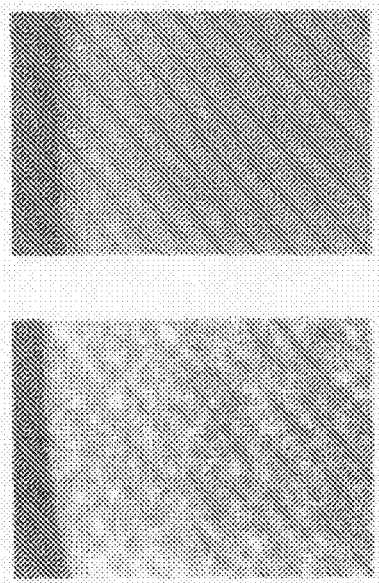

FIG. 23 is a fluorescence microscopic image of colon bacilli JM109 when an MPS surface layer of the colon bacilli JM109 coated with an MPS layer was modified with GFP. The upper in the figure shows colon bacilli not subjected to any coating treatment, and the lower therein shows colon bacilli subjected to the coating treatment (Example 23).

Figure 24:
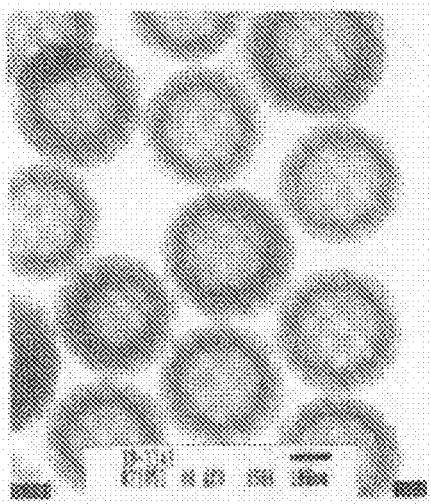

FIG. 24 is an electron microscopic image of liquid core organosilica shells wherein silica sells composed of MPS and TcPS were coated with a liquid (Example 24).

Figure 25:
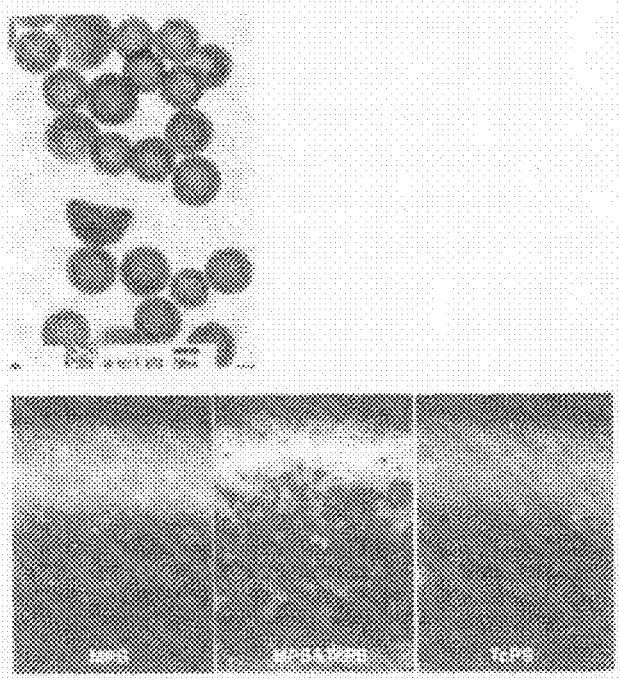

The upper in FIG. 25 is an electron microscopic image of liquid core organosilica shells wherein silica sells composed of MPS and TcPS were coated with a liquid. The lower in the figure show, from the left toward the right, a fluorescence microscopic image of particles made of MPS only, particles made of MPS and TcPS, and particles made of TcPS only and containing a fluorescent colorant (Example 25). (Example 25)

Figure 26:
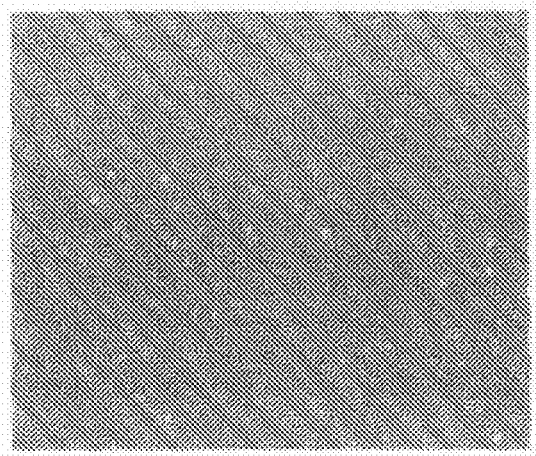

FIG. 26 is a fluorescence microscopic image an organosilica coat containing a fluorescent colorant in the surface of the silica (Example 26).

Figure 27:

FIG. 27 is a fluorescence microscopic image of an organosilica coat of a quantum dot (Example 27).

Figure 28:
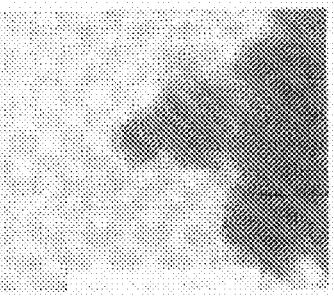
Figure 28:
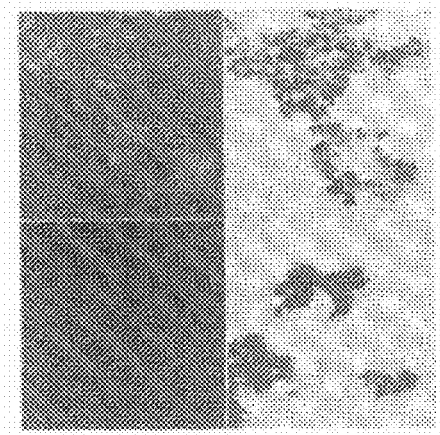

The upper in FIG. 28 is an electron microscopic image of a magnetic material coated with a silica shell layer composed of MPS and TcPS, and the upper stage of the lower in the figure is a fluorescence microscopic image of the coated particles bonded satisfactorily to GFP, and the lower stage thereof is a fluorescence microscopic image of uncoated particles (Example 28).

Figure 29:
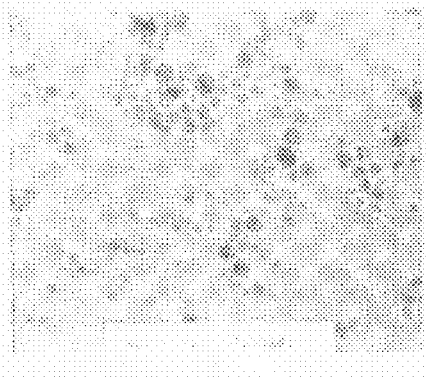

FIG. 29 is an electron microscopic image of another magnetic material coated with a silica shell layer composed of MPS and TcPS (Example 29).

Figure 30:
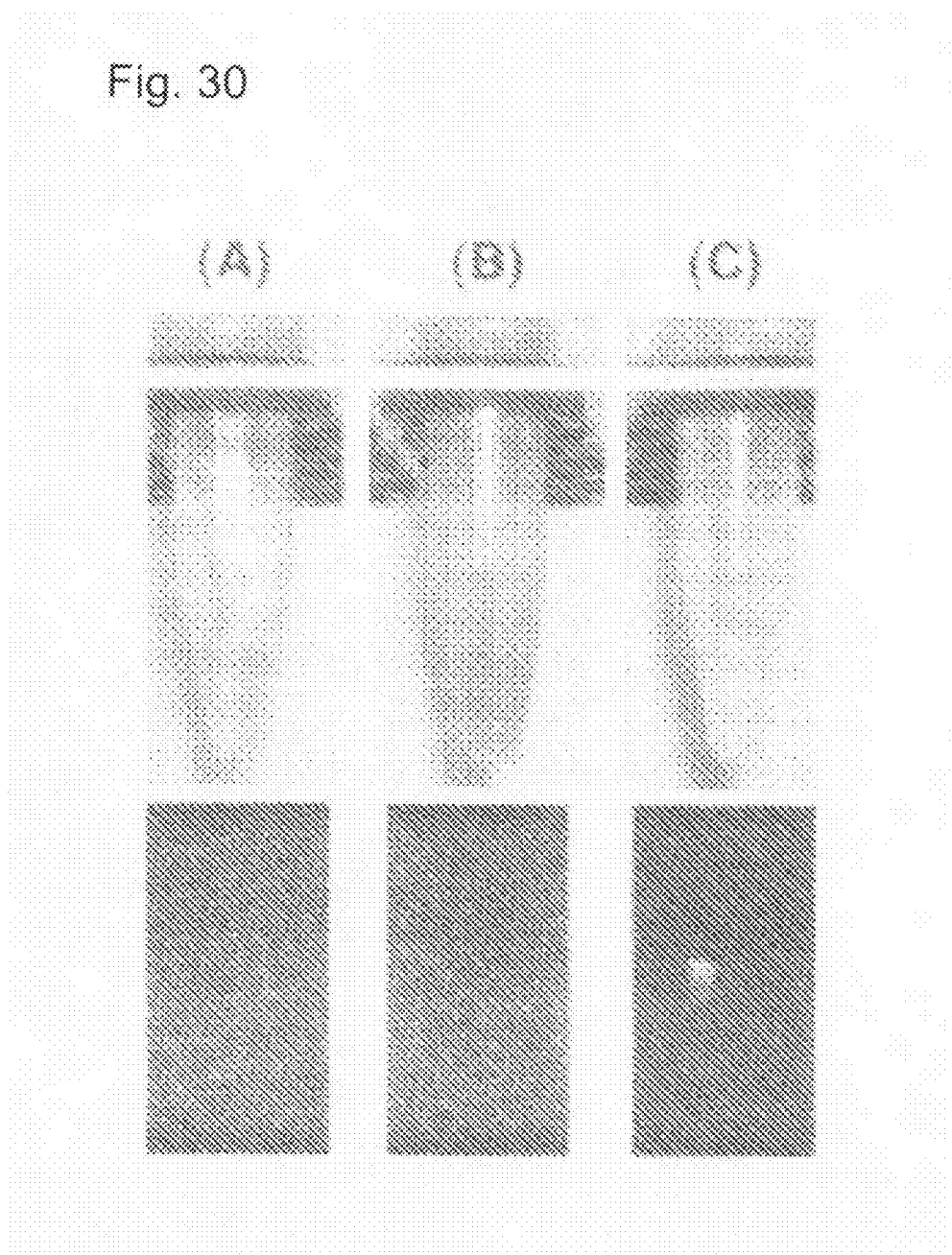

The upper in FIG. 30 shows an estimation of a magnetic material (A) of Example 18, which was coated with an MPS layer, an estimation of a magnetic material (B) of Example 29, which was coated with a layer of MPS and TcPS, and an estimation of liquid core organosilica shells (C) of Example 24, as a control, which was composed of MPS and TcPS and contained no magnetic material, the estimations being according to a compact MRI for small animals. The lower in the figure shows images each obtained by photographing nucleus particles put into a centrifugal tube under T2 emphasis conditions (Example 30).

Figure 31:
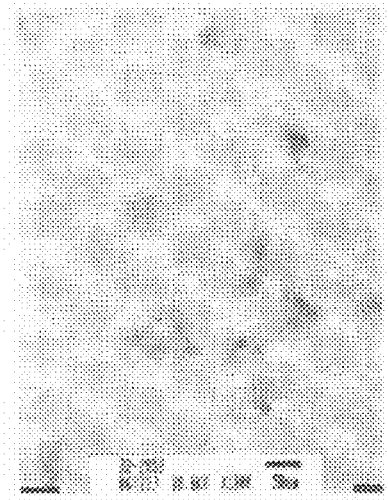

FIG. 31 is an electron microscopic image of hybrid particles composed of a quantum dot and a magnetic material coated with an MPS layer (Example 31).

Figure 32:
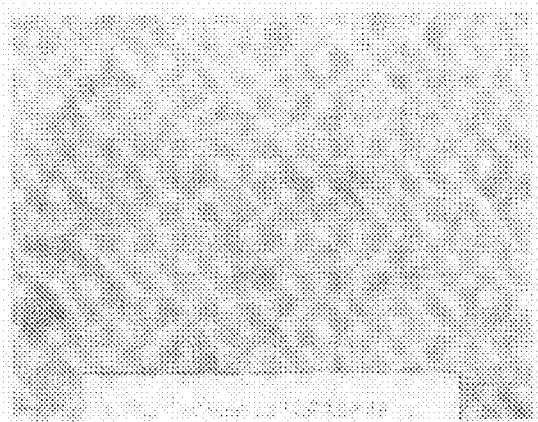

FIG. 32 is an electron microscopic image of organosilica particles containing a quantum dot and a magnetic material (Example 32).

Figure 33:
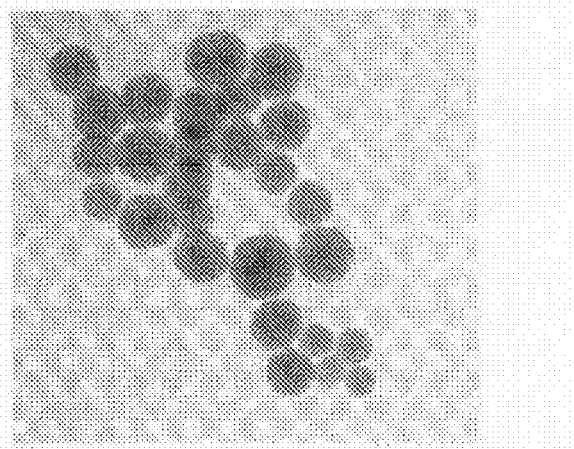

FIG. 33 is an electron microscopic image of a magnetic material coated with an APS/MPS layer (Example 33).

Figure 34:
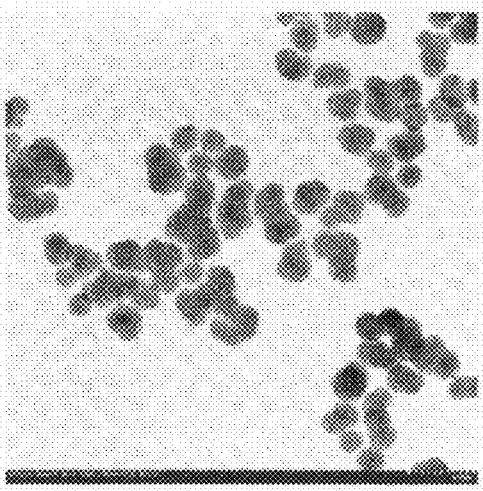

FIG. 34 is an electron microscopic image of a magnetic material coated with an MPS layer (Example 34).

Figure 35:
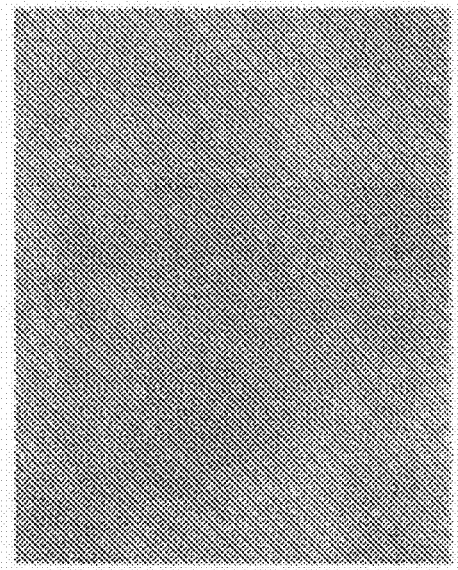

FIG. 35 is a fluorescence microscopic image of a magnetic material coated with an MPS layer (Example 34).

Figure 36:
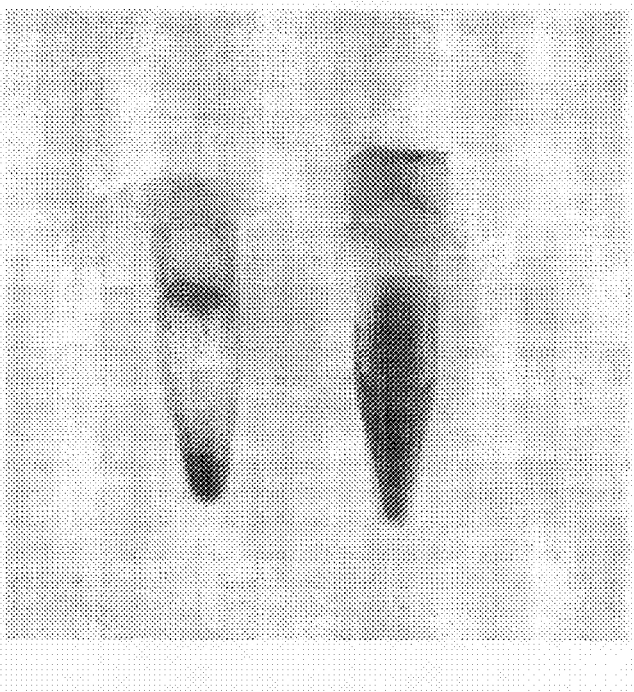

FIG. 36 is a view showing an aggregation/dispersion state of a magnetic material coated with an MPS layer before and after the coating (Example 34).

Figure 37:
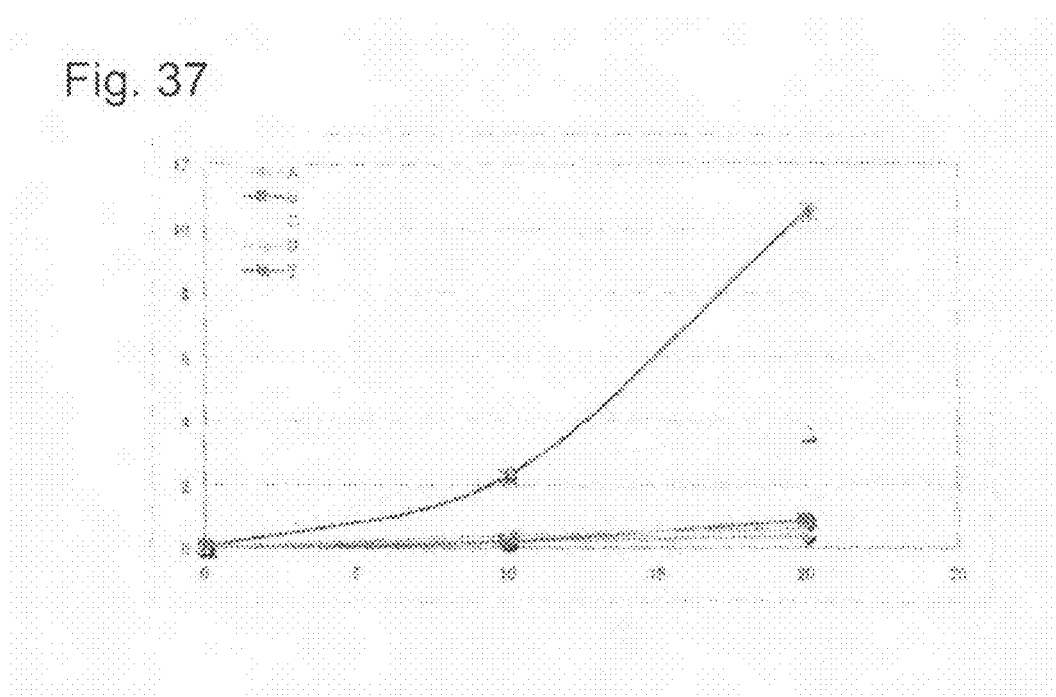

FIG. 37 shows measurement results obtained by mixing 5 μL of each of GFP solutions having various concentrations (0 to 40 μg/mL) with 5 μL of a solution of particles, diluting the mixture with 490 μL of distilled water, and measuring the diluted mixture by flow cytometry (Example 35).

Figure 38:
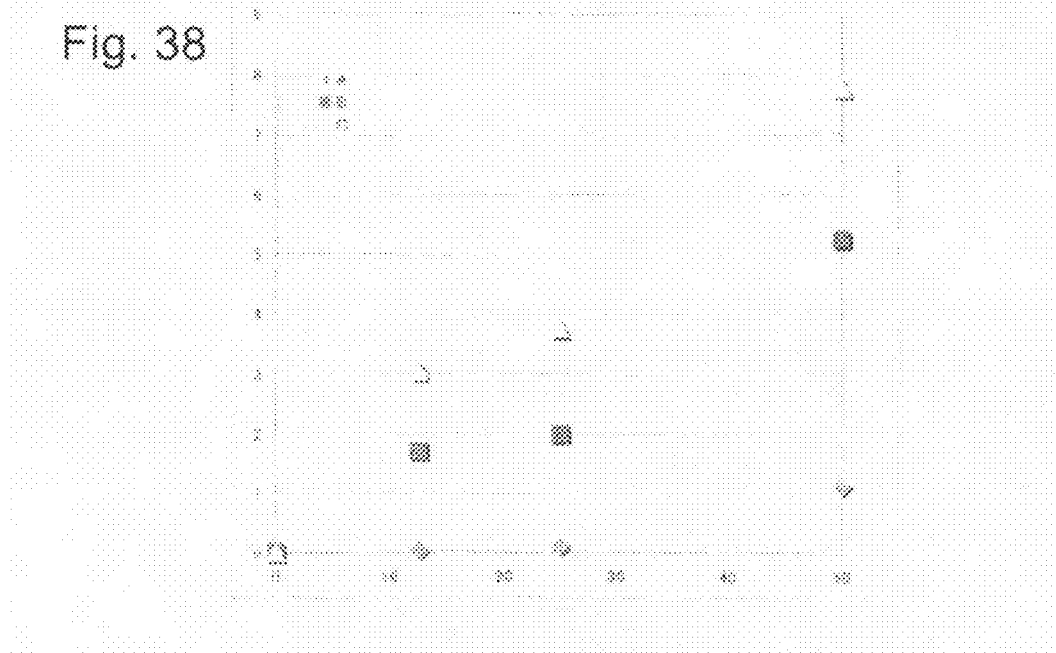

FIG. 38 shows measurement results obtained by mixing 5 μL of each of GFP solutions having various concentrations (0 to 50 μg/mL) with 5 μL of a solution of particles, allowing the reactive components to react with each other for 30 minutes, diluting the resultant with 470 μL of distilled water, and measuring the diluted solution by flow cytometry (Example 36).

Figure 39:
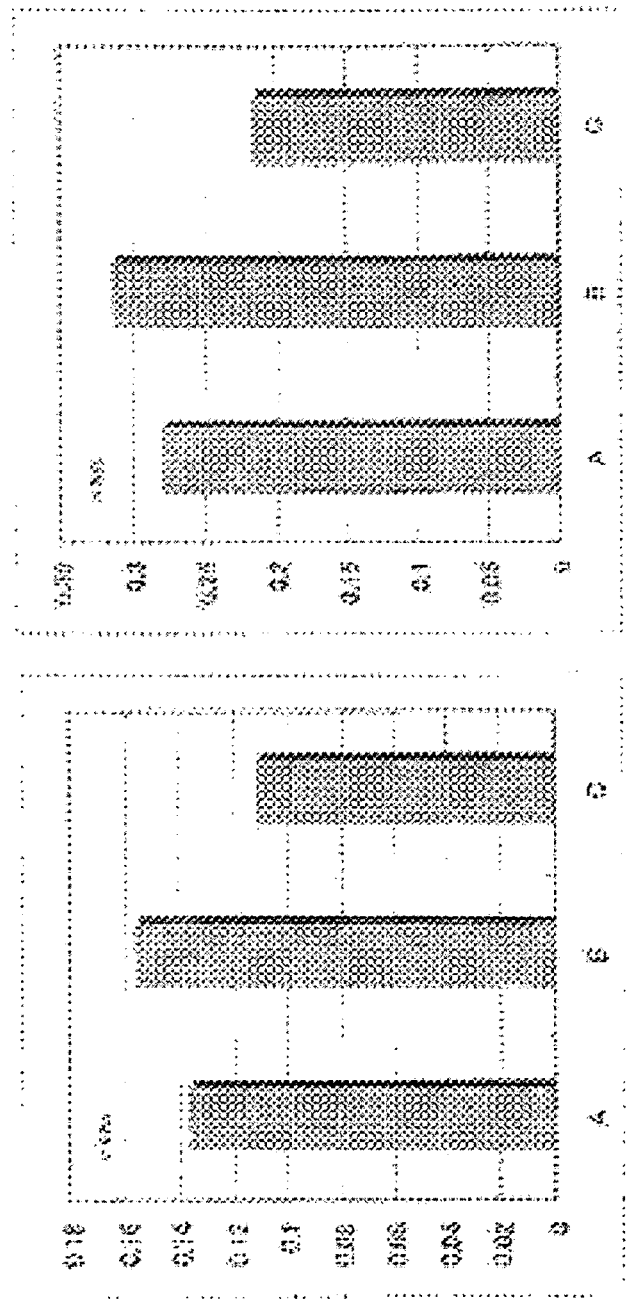

FIG. 39 is a figure wherein Table 7 is represented by as graphs, wherein the left graph is in the case of 30-minute cultivation in Example 38 and the right graph is in the case of 90-minute cultivation therein.

Figure 40:
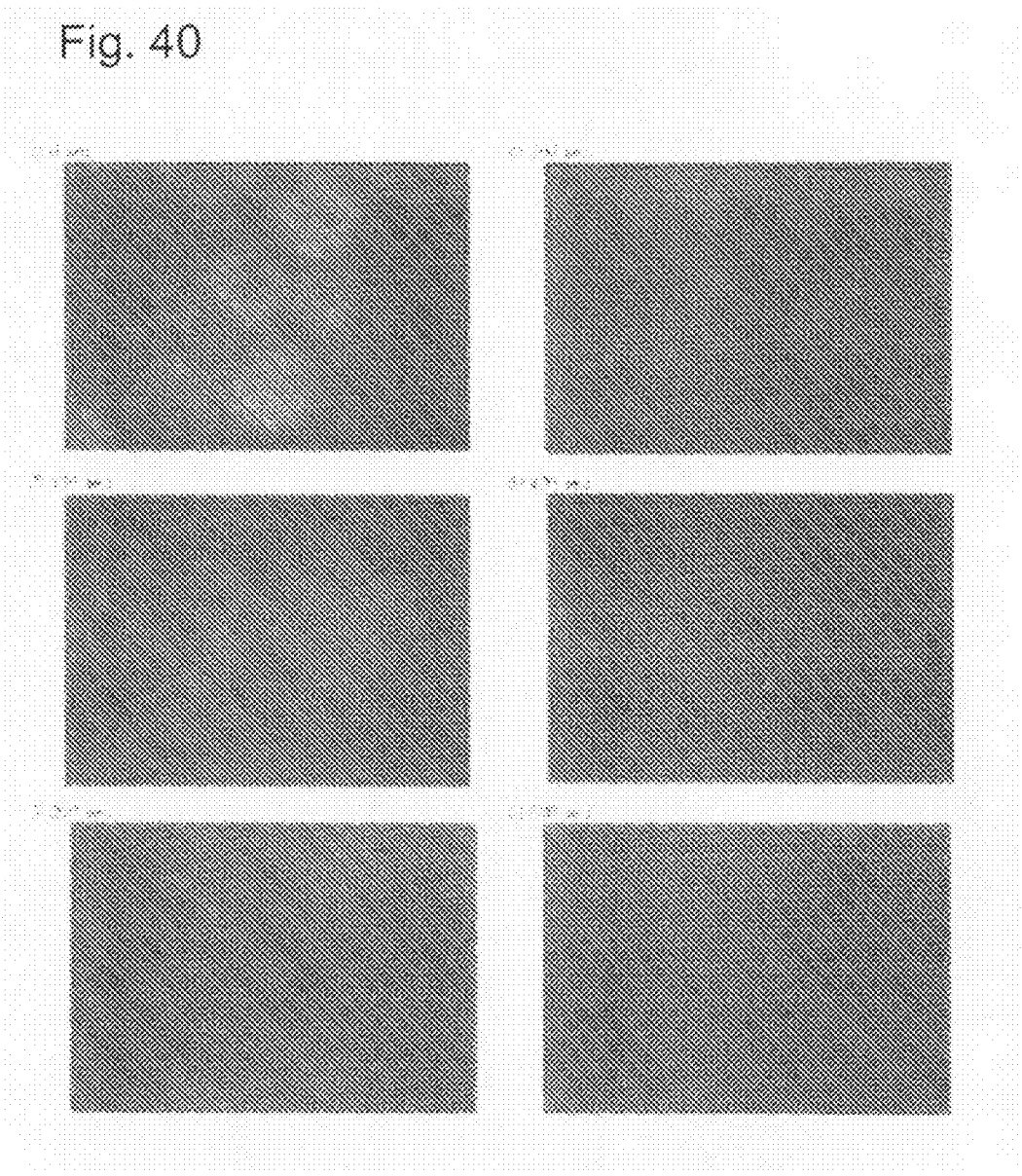

FIG. 40 is a fluorescence microscopic image obtained by arranging, along the passage of time, a change in the form of cells irradiated with excited light rays (528-553 nm) under a fluorescence microscope (Example 38).

What is claimed is:

1. Nanofunctional non-porous silica particles, comprising a shell made mainly of silica obtained from one or more organosilica compounds selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TCPS), acryloxypropyl trimethoxysilane (ACPS), aminopropyl trimethoxysilane (APS), and aminopropyl triethoxysilane (APES); and a core, in the shell, having a diameter of 2 to 200 nm and containing one or more species selected from the group consisting of a magnetic material, gold colloid, a quantum dot, gadolinium-containing particles, and an imaging functional material-containing liquid, wherein a thickness of the shell is more than 5 nm and less than 100 nm and wherein a functional compound chosen from fluorescent material or an imaging agent is held in the shell and in the core.

2. The nanofunctional non-porous silica particles according to claim 1, wherein the shell is made of two or more organosilica compounds selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TCPS), acryloxypropyl trimethoxysilane (ACPS), aminopropyl trimethoxysilane (APS), and aminopropyl triethoxysilane (APES).

3. The nanofunctional non-porous silica particles according to claim 1, wherein the thickness of the shell is more than 5 nm and less than 30 nm.

4. The nanofunctional non-porous silica particles according to claim 1, wherein a difference in surface potential between the shell and the functional compound itself is 3 mV or more.

5. The nanofunctional non-porous silica particles according to claim 1, wherein each of the nanofunctional non-porous silica particles have a particle diameter of 3 to 500 nm.

6. The nanofunctional non-porous silica particles according to claim 1, wherein a material having a cell damage activating function is held in the surface of the shell, and/or in the shell, and/or in the core.

7. The nanofunctional non-porous silica particles according to claim 6, wherein the material is irradiated with light to exhibit the cell damage activating function.

8. A method for manufacturing nanofunctional non-porous silica particles as recited in claim 1, comprising steps for:
(a) preparing a mixed liquid of an organosilica compound, a functional material, and an aqueous ammonia solution; or preparing a mixed liquid of an organosilica compound, a functional material, a functional compound, and an aqueous ammonia solution, and
(b) allowing the organosilica compound and the aqueous ammonia solution to react with one another at a predetermined temperature, wherein
the organosilica compound is one or more selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TcPS), acryloxypropyl trimethoxysilane (ACPS) and aminopropyl trimethoxysilane (APS),
the functional material is one or more species selected from the group consisting of a magnetic material, gold colloid, a quantum dot, gadolinium-containing particles, and an imaging functional material-containing liquid, and wherein
the aqueous ammonia solution and conditions for the temperature in the steps (a) and (b) are adjusted to satisfy the following:
(i) the temperature is high temperature (in the temperature range of 80 to 100° C.), and
(ii) the solution has high ammonia concentration (the solution gives a final concentration of 25% or more).

9. A method for manufacturing nanofunctional non-porous silica particles as recited in claim 1, comprising steps for:
(a) preparing a mixed liquid of organosilica compounds, a functional material, and an aqueous ammonia solution; or preparing a mixed liquid of organosilica compounds, a functional material, a functional compound, and an aqueous ammonia solution, and
(b) allowing the organosilica compounds and the aqueous ammonia solution to react with each other at a predetermined temperature, wherein
the organosilica compounds are one or more selected from the group consisting of mercaptopropyl trimethoxysilane (MPS), mercaptopropyl triethoxysilane (MPES), mercaptopropyl methyldimethoxysilane (MPDMS), trimethoxy[2-(7-oxabicyclo[4.1.0]-hept-3-yl)ethyl]silane (EpoPS), thiocyanatopropyl triethoxysilane (TcPS), acryloxypropyl trimethoxysilane (ACPS) and aminopropyl trimethoxysilane (APS), and aminopropyl triethoxysilane (APES),
the functional material is one or more species selected from the group consisting of a magnetic material, gold colloid, a quantum dot, gadolinium-containing particles, and an imaging functional material-containing liquid, and wherein
the aqueous ammonia solution and conditions for the temperature in the steps (a) and (b) are adjusted to satisfy the following:

(i) the temperature is high temperature (in the temperature range of 80 to 100° C.), and
(ii) the solution has a high ammonia concentration (the solution gives a final concentration of 25% or more).

* * * * *